United States Patent [19]

Pasteris

[11] Patent Number: 4,492,596
[45] Date of Patent: Jan. 8, 1985

[54] PHENYL-SUBSTITUTED SULFONAMIDES

[75] Inventor: Robert J. Pasteris, Wilmington, Del.

[73] Assignee: E. I. Du Pont De Nemours and Company, Wilmington, Del.

[21] Appl. No.: 406,191

[22] Filed: Aug. 11, 1982

[51] Int. Cl.$^3$ ............... C07D 407/12; C07D 409/12; A01N 43/54

[52] U.S. Cl. ............................................. 71/90; 71/91; 71/92; 544/209; 544/212; 544/278; 544/292; 544/321; 544/331; 544/332; 544/323; 544/324

[58] Field of Search ............... 544/319, 320, 321, 331, 544/332; 71/92, 90, 91

[56] References Cited

U.S. PATENT DOCUMENTS

| | | | |
|---|---|---|---|
| 4,368,067 | 1/1983 | Budzinski | 71/93 |
| 4,369,320 | 1/1983 | Levitt et al. | 544/320 |
| 4,398,939 | 8/1983 | Levitt | 71/90 |

Primary Examiner—Robert Gerstl

[57] ABSTRACT

This invention relates to 1-benzopyransulfonamides, 1-benzothiopyransulfonamides, 1-benzoxepinsulfonamides and 1-benzothiepinsulfonamides which are useful as plant growth regulants and in particular as herbicides.

54 Claims, No Drawings

PHENYL-SUBSTITUTED SULFONAMIDES

BACKGROUND OF THE INVENTION

This invention relates to 1-benzopyransulfonamides, 1-benzothiopyransulfonamides, 1-benzoxepinsulfonamides and 1-benzothiepinsulfonamides which are useful as plant growth regulants and in particular as herbicides.

Netherlands Pat. No. 121,788, published Sept. 15, 1966, discloses the preparation of compounds of the following Formula and their use as general or selective herbicides:

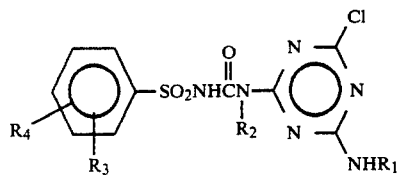

wherein
- $R_1$ and $R_2$ may independently be alkyl of 1–4 carbon atoms; and
- $R_3$ and $R_4$ may independently be hydrogen, chlorine or alkyl of 1–4 carbon atoms.

U.S. Pat. No. 3,637,366 discloses compounds having the formula:

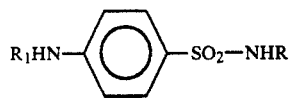

wherein:
- $R_1$ is hydrogen or lower saturated aliphatic acyl and
- $R_2$ is hydrogen, 2-pyrimidinyl, pyridyl, amidino, acetyl or carbamoyl.

The disclosed compounds are said to provide control of crabgrass, cress, endive, clover and *Poa annua*.

French Pat. No. 1,468,747 discloses the following para-substituted phenylsulfonamides as being useful as antidiabetic agents:

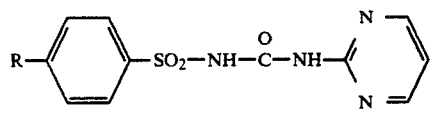

wherein R=H, halogen, $CF_3$ or alkyl.

Logemann et al., Chem. Ab., 53, 18052g (1959), disclose a number of sulfonamides, including uracil derivatives and those having the formula:

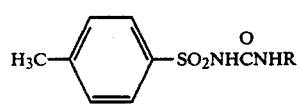

wherein
R is butyl, phenyl or

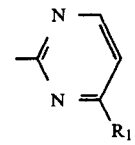

and
$R_1$ is hydrogen or methyl.

When tested for hypoglycemic effect in rats (oral doses of 25 mg/100 g), the compounds in which R is butyl and phenyl were most potent. The others were of low potency or inactive.

Wojciechowski, J. Acta. Polon. Pharm. 19, p. 121–5 (1962) [Chem. Ab., 59 1633 e] describes the synthesis of N-[(2,6-dimethoxypyrimidin-4-yl)aminocarbonyl]-4-methylbenzenesulfonamide:

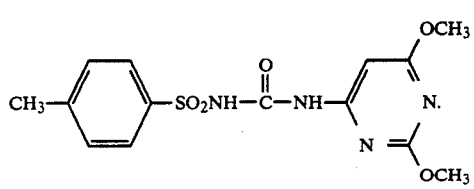

U.S. Pat. No. 4,127,405 teaches compounds which are useful for controlling weeds in wheat having the formula

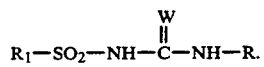

wherein R is

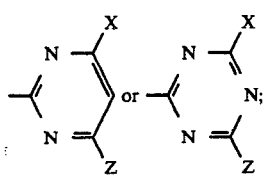

$R_1$ is

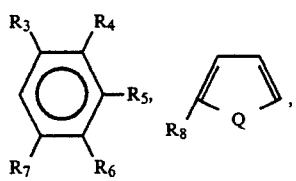

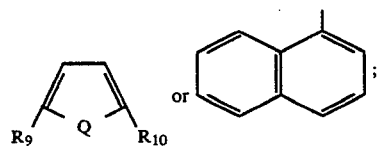

$R_3$ and $R_6$ are independently hydrogen, fluorine, chlorine, bromine, iodine, alkyl of 1–4 carbon atoms, alkoxy of 1–4 carbon atoms, nitro, trifluoromethyl, cyano, $CH_3S(O)_n-$ or $CH_3CH_2S(O)_n-$;

$R_4$ is hydrogen, fluorine, chlorine, bromine or methyl;

$R_5$ is hydrogen, fluorine, chlorine, bromine, methyl or methoxy;

$R_7$ is hydrogen, fluorine, chlorine, bromine, alkyl of 1–2 carbon atoms or alkoxy of 1–2 carbon atom;

$R_8$ is hydrogen, methyl, chlorine or bromine;

$R_9$ and $R_{10}$ are independently hydrogen, methyl, chlorine or bromine;

W and Q are independently oxygen or sulfur;

n is 0, 1 or 2;

X is hydrogen, chlorine, bromine, methyl, ethyl, alkoxy of 1–3 carbon atoms, trifluoromethyl, $CH_3S-$ or $CH_3OCH_2-$; and Z is methyl or methoxy;

or their agriculturally suitable salts; provided that:

(a) when $R_5$ is other than hydrogen, at least one of $R_3$, $R_4$, $R_6$ and $R_7$ is other than hydrogen and at least two of $R_3$, $R_4$, $R_6$ and $R_7$ must be hydrogen;

(b) when $R_5$ is hydrogen and all of $R_3$, $R_4$, $R_6$ and $R_7$ are other than hydrogen, then all of $R_3$, $R_4$, $R_6$ and $R_7$ must be either chlorine or methyl; and (c) when $R_3$ and $R_7$ are both hydrogen, at least one of $R_4$, $R_5$ or $R_6$ must be hydrogen.

In addition, U.S. Ser. No. 227,886 teaches o-alkylsulfonylbenzenesulfonylureas which are useful as herbicides.

In U.S. Ser. No. 274,233, there is a disclosure of herbicidal benzo[b]thiophene- and benzofuransulfonylureas in which the sulfonylureido group is bonded to the heterocyclic ring.

In U.S. Ser. No. 363,379, there is a disclosure of herbicidal benzodioxole- and benzodioxansulfonylureas, while in U.S. Ser. No. 312,183, herbicidal benzofuran- and benzothiophenesulfonylureas are disclosed in which thiosulfonylureido group is bonded to the benzo ring.

Undesired vegetation can cause substantial damage to useful crops, especially agricultural products that satisfy man's basic food and fiber needs, such as cotton, rice, corn, wheat, soybean and the like.

Although a wide variety of materials are available which can be used for killing or inhibiting (controlling) the growth of undesired vegetation the need exists for still more effective herbicides that destroy or control weeds without causing significant damage to useful crops.

SUMMARY OF THE INVENTION

This invention relates to compounds of Formula I, agricultural compositions containing them and their method-of-use as general or selective pre-emergent or post-emergent herbicides or plant growth regulants.

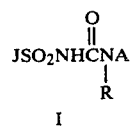

I wherein J is

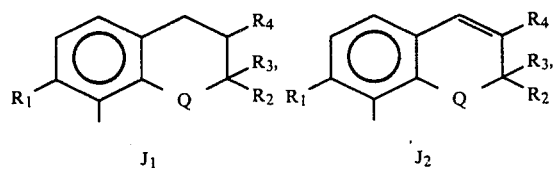

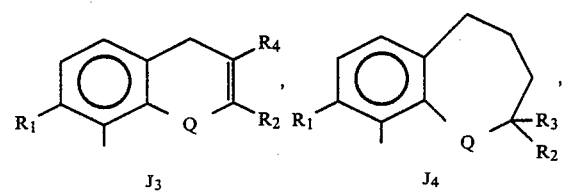

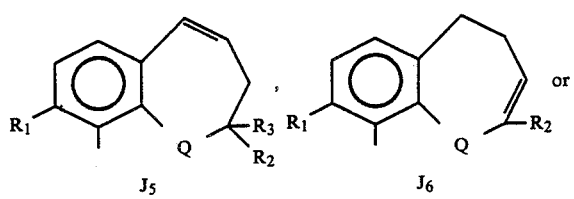

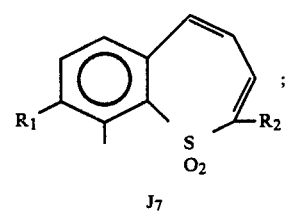

Q is O, S or $SO_2$;

R is H or $CH_3$;

$R_1$ is H, $CH_3$, $OCH_3$, Cl, Br, $CO_2R_5$, $SO_2R_6$, $OSO_2R_7$ or $SO_2NR_8R_9$;

$R_4$ is H or $CH_3$;

$R_2$ and $R_3$ are independently H or $C_1-C_3$ alkyl;

$R_5$ is $C_1-C_3$ alkyl, $CH_2CH=CH_2$, $CH_2CH_2OCH_3$ or $CH_2CH_2Cl$;

$R_6$ is $C_1-C_3$ alkyl;

$R_7$ is $C_1-C_3$ alkyl or $CF_3$;

$R_8$ and $R_9$ are independently $C_1-C_2$ alkyl;

A is

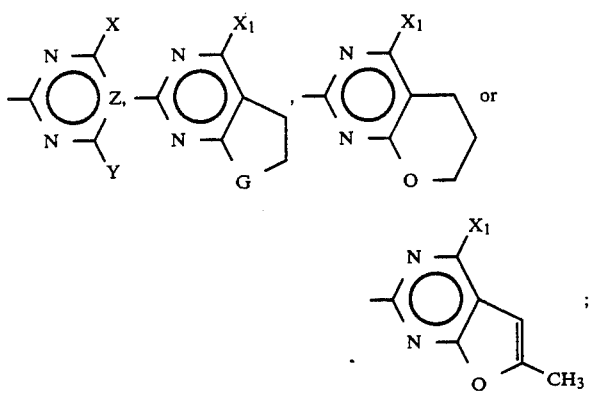

X is $CH_3$, $OCH_3$ or Cl;

Y is $CH_3$, $OCH_3$, $OC_2H_5$, $CH_2OCH_3$, $C_2H_5$, $NH_2$, $NHCH_3$ or $N(CH_3)_2$;

Z is CH or N;

G is O or $CH_2$; and $X_1$ is $CH_3$, $OCH_3$ or $OC_2H_5$;

and their agriculturally suitable salts; provided that:

(1) when X is Cl, then Z is CH and Y is $OCH_3$, $NH_2$, $NHCH_3$, $N(CH_3)_2$ or $OC_2H_5$;

(2) the total number of carbon atoms in $R_2$ and $R_3$ are less than or equal to 3;

(3) in Formula J₂, when R₂ and R₃ are other than H, then R₄ is H;
(4) in Formula J₃, when R₂ is other than H, then R₄ is H;
(5) when Q is S, then R₁ is not SO₂NR₈R₉;
(6) in Formulae J₃ and J₆, Q may not be O;
(7) in Formula J₇, R₁ is not CH₃.

Preferred for reasons of their higher herbicidal activity, greater plant growth regulant activity, or more favorable ease of synthesis are:

(1) Compounds of Formula I where J is J₁.
(2) Compounds of preferred 1 where R is H.
(3) Compounds of preferred 2 where R₁ is H.
(4) Compounds of preferred 3 where A is

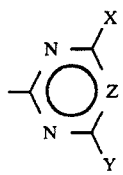

and X is OCH₃ or Cl.
(5) Compounds of preferred 4 where Y is CH₃ or OCH₃.
(6) Compounds of Formula I where J is J₂.
(7) Compounds of preferred 6 where R is H.
(8) Compounds of preferred 7 where R₁ is H.
(9) Compounds of preferred 8 where A is

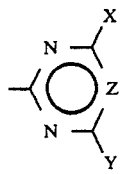

and X is OCH₃ or Cl.
(10) Compounds of preferred 9 where Y is CH₃ or OCH₃.
(11) Compounds of Formula I where J is J₃.
(12) Compounds of preferred 11 where R is H.
(13) Compounds of preferred 12 where R₁ is H.
(14) Compounds of preferred 13 where A is

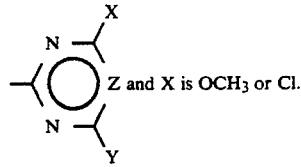

and X is OCH₃ or Cl.
(15) Compounds of preferred 14 where Y is CH₃ or OCH₃.
(16) Compounds of Formula I where J is J₄.
(17) Compounds of preferred 16 where R is H.
(18) Compounds of preferred 17 where R₁ is H.
(19) Compounds of preferred 18 where A is

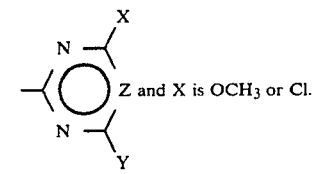

and X is OCH₃ or Cl.
(20) Compounds of preferred 19 where Y is CH₃ or OCH₃.
(21) Compounds of Formula I where J is J₅.
(22) Compounds of preferred 21 where R is H.
(23) Compounds of preferred 22 where R₁ is H.
(24) Compounds of preferred 23 where A is

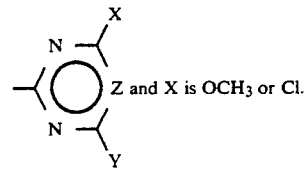

and X is OCH₃ or Cl.
(25) Compounds of preferred 24 where Y is CH₃ or OCH₃.
(26) Compounds of Formula I where J is J₆.
(27) Compounds of preferred 26 where R is H.
(28) Compounds of preferred 27 where R₁ is H.
(29) Compounds of preferred 28 where A is

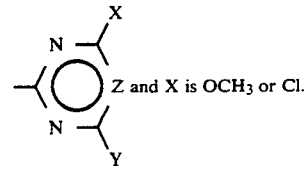

and X is OCH₃ or Cl.
(30) Compounds of preferred 29 where Y is CH₃ or OCH₃.
(31) Compounds of Formula I where J is J₇.
(32) Compounds of preferred 31 where R is H.
(33) Compounds of preferred 32 where R₁ is H.
(34) Compounds of preferred 33 where A is

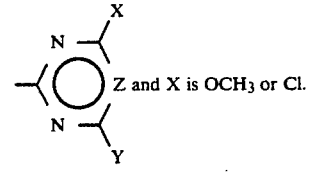

and X is OCH₃ or Cl.
(35) Compounds of preferred 34 where Y is CH₃ or OCH₃.

Specifically preferred for reasons of their highest herbicidal activity, greatest plant growth regulant activity and/or most favorable ease of synthesis are:
N-[(4-methoxy-6-methylpyrimidin-2-yl)aminocarbonyl]-3,4-dihydro-2H-1-benzothiopyran-8-sulfonamide, 1,1-dioxide;

N-[(4,6-dimethoxypyrimidin-2-yl)aminocarbonyl]-3,4-dihydro-2H-1-benzothiopyran-8-sulfonamide, 1,1-dioxide; and N-[(4-methoxy-6-methyl-1,3,5-triazin-2-yl)aminocarbonyl]-3,4-dihydro-2H-1-benzothiapyran-8-sulfonamide, 1,1-dioxide.

DETAILED DESCRIPTION OF THE INVENTION

Synthesis

The compounds of Formula (I) can be prepared by methods described below in Equations 1, 2 and 3.

As shown in Equation 1, compounds of Formula (I) can be prepared by reacting a sulfonylcarbamate of Formula (II) with an appropriate amine of Formula (III). J, R and A are as previously defined.

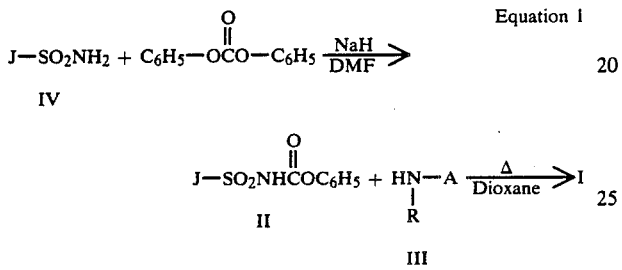

Equation 1

The reaction is carried out at 50°–100° C. in a solvent such as dioxane for ½ to 24 hours as taught in EPO Publication No. 44807. The required carbamates (II) are prepared by reacting the corresponding sulfonamides (IV) with diphenylcarbonate in the presence of a strong base.

Alternatively, as shown in Equation 2, compounds (I), where $R_1$ is other than $CO_2R_5$, can be prepared by reacting sulfonamides of Formula (IV) with an appropriate methylcarbamate of Formula (V) in the presence of an equimolar amount of trimethylaluminum.

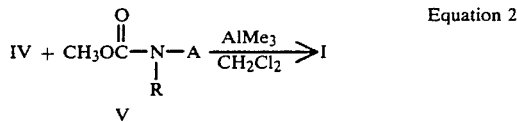

Equation 2

The reaction is carried out at 25° to 40° C. in a solvent such as methylene chloride for 10 to 96 hours under an inert atmosphere as taught in U.S. Ser. No. 337,934.

The compounds of Formula (I) where J is $J_1$, $J_4$ and $J_7$ for all values of Q and $J_2$, $J_3$, $J_5$ and $J_6$ when Q is $SO_2$ can be prepared by reacting sulfonylisocyanates of Formula (VI) with an appropriate amine of Formula (III) as shown in Equation 3.

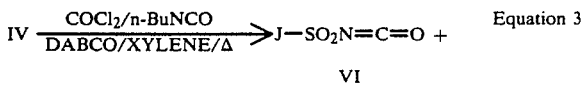

Equation 3

III $\xrightarrow{\text{solvent}}$ I

The reaction is carried out at 25° to 40° C. in an inert aprotic solvent such as methylene chloride for 0.5 to 24 hours as taught in U.S. Pat. No. 4,127,405. The intermediate sulfonylisocyanates (VI) can be prepared from the appropriate sulfonamides (IV) by the reaction with phosgene, in the presence n-butylisocyanate and a tertiary amine catalyst, at reflux in a solvent such as xylene by the method of U.S. Pat. No. 4,238,621.

Alternatively, the sulfonylisocyanates can be prepared from the sulfonamides by a two step procedure involving (a) reacting the sulfonamides with n-butylisocyanate in the presence of a base such as $K_2CO_3$ at reflux in an inert solvent such as 2-butanone forming a n-butylsulfonylurea; and (b) reacting this compound with phosgene and a tertiary amine catalyst at reflux in xylene solvent. The method is similar to a procedure taught by Ulrich and Sayigh, Newer Methods of Preparative Organic Chemistry, Vol. VI, p. 223–241, Academic Press, New York and London, W. Foerst Ed.

The sulfonamides of Formula IV in Equations 1, 2 and 3 are important intermediates for the preparation of the compounds of this invention. The synthesis of the required sulfonamide intermediates are described in Equations 4, 5 and 6.

As shown in Equation 4, sulfonamides of Formula IV, where J is $J_1$, $J_2$, $J_4$, $J_5$ and $J_7$ for all Q, can be prepared from the corresponding sulfonyl chlorides of Formula VII.

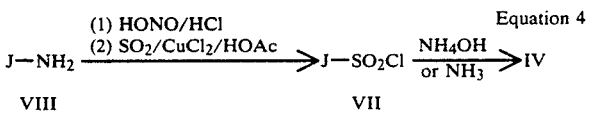

Equation 4

The preparation of sulfonamides from ammonium hydroxide and sulfonyl chlorides is widely reported in the literature, e.g., Crossley et al., J. Am. Chem. Soc., 60, 2223 (1938) and Pailer, Monatsh., 92, 677 (1961). Preparation utilizing the reaction of sulfonyl chlorides with an excess of anhydrous ammonia at 0° C. in ethyl ether or chlorobutane is also known.

The sulfonyl chlorides VII can be prepared from the appropriate amine VIII by diazotization with sodium nitrite in HCl, followed by reaction of the diazonium salt with sulfur dioxide and cupric chloride in acetic acid analogous to the teachings of Yale and Sowinski, J. Org. Chem., 25, 1824 (1960).

Alternatively, sulfonyl chlorides of Formula VII can be prepared by a modification of the above procedure whereby the diazotization reaction is carried out in dilute sulfuric acid and the resulting diazonium salt is reacted with sulfur dioxide, HCl and cupric chloride in a cosolvent mixture consisting of acetic acid-water (1:1) and an immiscible, inert solvent such as 1-chlorobutane or methylene chloride at 0°–40° C. for 1 to 24 hours as disclosed by the teachings of U.S. Ser. No. 345,935.

Sulfonamides of Formula IVa, where n is 1 or 2, are prepared from their corresponding saturated analogs IVb as shown in Equation 5. $R_1$, $R_2$, and $R_4$ are as previously defined. When n is 2, $R_4$ is H.

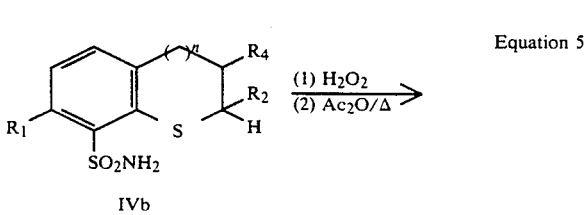

Equation 5

-continued

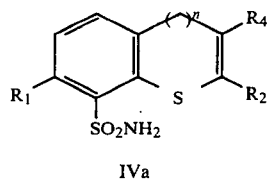

IVa

The reaction is carried out by contacting the saturated sulfide with one equivalent of a suitable oxidizing agent such as hydrogen peroxide in a solvent such as acetic acid to produce the corresponding sulfoxide. The sulfoxide is then heated with acetic anhydride with or without a cosolvent at 50° to 140° C. for 2 to 24 hours. This is similar to the method taught by Parham and Koncos, *J. Amer. Chem. Soc.*, 83, 4034 (1961) for the preparation of 4H-1-benzothiopyran.

Sulfonamides of Formula IVc where n is 0 or 1 can also be prepared from the corresponding saturated analogs IVd by the two step sequence shown in Equation 6. $R_1$, $R_2$, $R_3$, $R_4$ and Q are as previously described except that $R_1$ is not $CH_3$. When n is 1, $R_4$ is H.

Equation 6

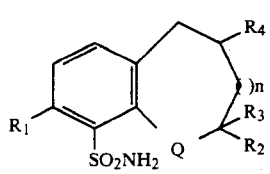 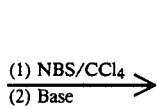

IVd

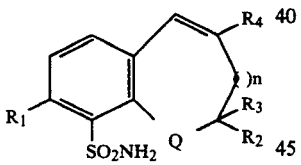

IVc

The first step involves benzylic bromination by N-bromosuccinimide in refluxing carbon tetrachloride to give a monobromo derivative. The monobromide is dehydrobrominated in the second step by contacting with a suitable base such as DABCO or ethoxide in an inert solvent such as benzene. This method has been used to prepare 2H-1-benzopyran from dihydrobenzopyran (Clemo and Ghatge, *J. Chem. Soc.*, 4347 (1955)).

Applying the above procedure a second time to the compounds IVc where n is 1, Q is $SO_2$ and $R_3$ is H will provide sulfonamides IV where J is $J_7$, as taught by Traynelis and Love, *J. Org. Chem.*, 26, 2728 (1961).

Finally, sulfonamides of Formula IV where Q is $SO_2$ can be prepared from the appropriate sulfonamides IV where Q is S by a variety of standard literature procedures with m-chloroperbenzoic acid (Johnson et. al., *Tetrahedron* 25, 5649 (1969), or with aqueous hydrogen peroxide in acetic acid (Bordwell et. al., *J. Amer. Chem. Soc.*, 77, 1141 (1955)).

The amines of Formula VIII in Equation 4, where J is $J_1$, $J_2$, $J_4$, $J_5$ and $J_7$ for all Q, can be prepared by reduction of the corresponding nitro compounds of Formula IX, as shown in Equation 7.

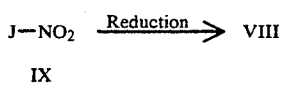

Equation 7

The reduction of nitro compounds to amines can be carried out by any of several known methods as described in *Preparative Organic Chemistry*, 4 Ed., p. 557–563, John Wiley and Sons, New York and London, G. Hilgetag and A. Martini Ed.

Alternatively, the amines of Formula VIIIa can be prepared by a thioClaisen rearrangement of an appropriate allyl phenylthio ether X as outlined in Equation 8. $R_1$, $R_2$, $R_3$ and $R_4$ are as previously defined.

Equation 8

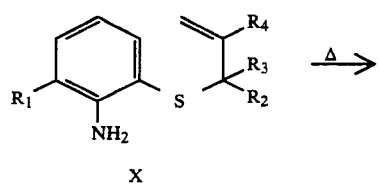

X

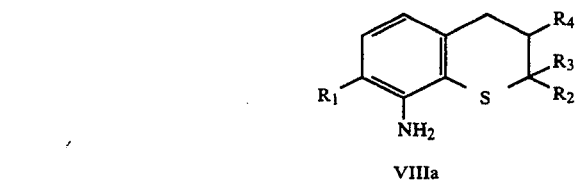

VIIIa

The rearrangements are carried out at 180° to 250° C. for 0.5 to 24 hours either neat or in the presence of a high boiling amine solvent such as quinoline or diethylaniline as taught by S. J. Rhoads and N. R. Raulins, *Organic Reactions*, Vol. 22, p. 1–252, John Wiley and Sons, New York and London, W. G. Dauben, Editor in Chief. In certain cases, the 6-ring fused product VIIIa is accompanied by a 5-ring fused isomer. The desired amine VIIIa can be separated by either fractional crystallization, fractional distillation or by a chromatographic method. The starting allylphenylthio ethers X can be prepared from the appropriate aminothiophenols by methods known to one skilled in the art.

The preparation of the nitro compounds of Formula IX in Equation 7 where J is either $J_1$ and $J_4$ or $J_2$ and $J_5$ and $R_1$ is H, $CH_3$, $OCH_3$, Cl or Br is outlined in Equation 9. The two routes utilize a common nitro ketone intermediate XI; $R_2$, $R_3$, $R_4$ and Q are as previously defined and n is 0 or 1; when n is 1, $R_4$ is H.

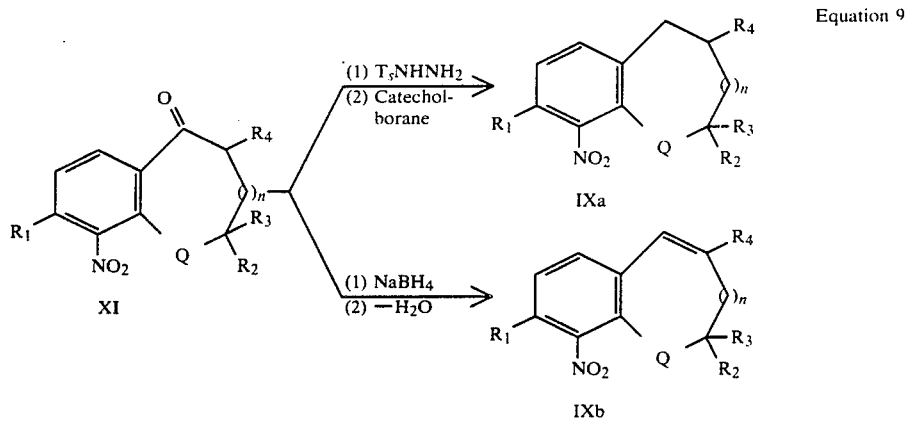

Equation 9

The saturated nitro compounds of Formula Xa are prepared by selectively reducing the tosylhydrozone derivative of nitro ketone XI with catecholborane in a solvent such as chloroform for 2 to 24 hours at ambient temperatures according to the teachings of Kabalka and Chandler, *Synthetic Commun.*, 9, 275 (1979).

Alternatively, ketone XI can be reduced directly to give the corresponding alcohol which is then dehydrated by one of a variety of known methods such as $P_2O_5$ by one skilled in the art.

The nitro compounds of Formula IX in Equation 7 where J is $J_1$ and $J_4$ and $R_1$ is $CO_2R_5$, $SO_2R_6$, $OSO_2R_7$ or $SO_2NR_8R_9$ are prepared from the corresponding compounds IXc (from Equation 9, compounds IXa where $R_1$ is Cl) as shown in Equation 10. $R_2$, $R_3$ and $R_4$ are as previously defined, Q is O or S and n is 0 or 1; when n is 1, and $R_4$ is H.

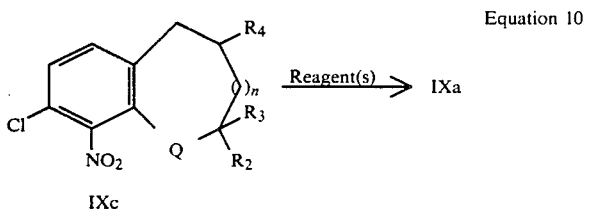

Equation 10

As shown in Equation 10, the chloronitro compounds IXc are contacted with a reagent or reagents, to be discussed below, to form compounds IXa containing the desired $R_1$ group.

The nitro compounds of Formula IXa where $R_1$ is $SO_2R_6$ are prepared in one step by reacting IXc with an appropriate sulfinic acid salt in a solvent such as dimethylformamide at 25° to 80° C. for 1 to 24 hours. Such displacements are reviewed in *Organic Chemistry of Sulfur*, p. 536–539, Plenum Press, New York and London, 1977, S. Oae, Ed. Alternatively, IXc can be reacted with an appropriate thiol in the presence of a suitable base such as sodium hydride or potassium hydroxide under the conditions described above to give an intermediate sulfide of Formula IXa where $R_1$ is $SR_6$. The sulfide is then oxidized to the desired compounds IXa where $R_1$ is $SO_2R_8$ and Q is O or $SO_2$ by methods known to one skilled in the art.

The nitro compounds of Formula IXa where $R_1$ is $SO_2NR_8R_9$ and Q is O or $SO_2$ are prepared in two steps starting from an intermediate sulfide (IXa where $R_1$ is $SR_6$) prepared as described above. The sulfide is reacted with molecular chlorine in aqueous acetic acid at 10° to 50° C. for 0.5 to 4 hours to give the corresponding sulfonyl chloride IXa where $R_1$ is $SO_2Cl$ as taught by Langler, *Can. J. Chem.*, 54, 498 (1976) and Langler and Grossert, *Can. J. Chem.*, 55, 407 (1977). The sulfonyl chloride is then contacted with an excess of an appropriate dialkyl amine in an inert solvent such as tetrahydrofuran by methods known to one skilled in the art.

The nitro compounds of Formula IXa where $R_1$ is $OSO_2R_7$ can be prepared in two steps by first heating IXc with one equivalent of a strong base such as sodium or potassium hydroxide in dimethylformamide at 25° to 80° C. for 1 to 8 hours to form an intermediate compound IXa where $R_1$ is OH. This intermediate is reacted with an appropriate sulfonyl chloride $R_8SO_2Cl$ or the appropriate anhydride in the presence of a base such as triethyl amine in an inert solvent such as methylene chloride at 0° to 40° C. for 1 to 24 hours.

The nitro compounds of Formula IXa where $R_1$ is $CO_2R_5$ can be prepared in three steps by first reacting IXc with one equivalent of potassium cyanide in dimethylformamide at 25° to 80° C. for 1 to 8 hours to form an intermediate compound IXa where $R_1$ is CN. This intermediate can be hydrolized by heating in a strong acid such as HCl in a solvent such as acetic acid to form a carboxylic acid which can then be converted to its corresponding esters by methods known to one skilled in the art.

The nitro compounds of Formula IX in Equation 7 where J is $J_2$ and $J_5$ (Formula IXb in Equation 9) and $R_1$ is $CO_2R_5$, $SO_2R_6$, $OSO_2R_7$ or $SO_2NR_8R_9$ are prepared from the corresponding saturated analogs IXa by the bromination/dehydrobromination sequence described earlier for sulfonamides IVc in Equation 6. This procedure can also be used to prepare compounds of Formula IXb where $R_1$ is H, $OCH_3$, Cl or Br. When this procedure is applied a second time to compounds IXb where n is 1, Q is $SO_2$ and $R_3$ and $R_4$ are H, the nitro compounds of Formula IX where J is $J_7$ are obtained.

Finally, the nitro compounds of Formula IX in Equation 7 where Q is $SO_2$ can be prepared from the corresponding nitro compound IX where Q is S by methods discussed earlier for sulfonamides IV.

Several of the nitro compounds of Formula IX are known, for example 8-nitro-3,4-dihydro-2H-1-benzopyran (Bowie and Chai, *Aust. J. Chem.*, 30, 675 (1977)), and 8-nitro-2H-1-benzopyran (Box and McCaw, *Rev. Latinoam. Quim.*, 10, 118, (1979)).

The nitro ketones of Formula XI in Equation 10 where $R_1$ is H, $CH_3$, $OCH_3$, Cl or Br are prepared by cyclization of the appropriate carboxylic acid XII as shown in Equation 11. $R_2$, $R_3$ and $R_4$ are as previously defined, Q is O or S and n is 0 or 1, when n is 1, $R_4$ is H.

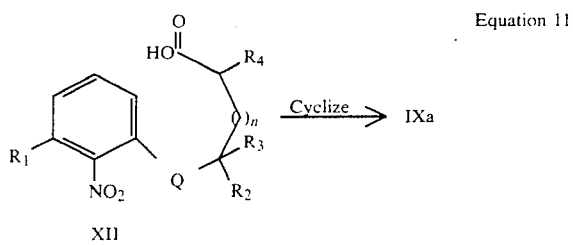

Equation 11

The reaction is carried out by heating the acid with a suitable condensing agent such as polyphosphoric acid, hydrofluoric acid, sulfuric acid or stannic chloride or the acid may be converted to its chloride and heated with a typical Friedel-Crafts reagent such as aluminum chloride or stannic chloride. For a comprehensive review of this and related reactions, see "Friedel-Crafts and Related Reactions" Vols. 1–4, Interscience, New York and London, G. A. Olah, Ed.

In cases where $R_2$ does not equal $R_3$, and $R_4$ is other than H, isomeric mixtures may result. These mixtures can be used in subsequent reactions or separated by fractional crystallization or chromatographic methods.

The starting nitro carboxylic acids XII can be prepared by reacting an appropriate nitrophenol or nitrothiophenol with the appropriate β-bromopropionate or γ-bromobutyrate in the presence of base by methods known to one skilled in the art. The preparation of benzopyrans, benzothiopyrans, benzoxepin and benzothiepin from substituted phenols and thiophenols are widely reported in the literature. For general reviews see "Chromans and Tocopherols", *The Chemistry of Heterocyclic Compounds*, Vol. 36, John Wiley and Sons, New York, 1981, G. P. Ellis, ED.; "Chromenes, Chromanones and Chromones", *The Chemistry of Heterocyclic Compounds*, Vol. 31, John Wiley and Sons, New York, 1977, G. P. Ellis, Ed.; "Seven-Membered Heterocyclic Compounds Containing Oxygen and Sulfur", *The Chemistry of Heterocyclic Compounds*, Vol. 26, John Wiley and Sons, New York, 1972, A. Rosowsky, Ed.; "Polycyclic Five- and Six-Membered Compounds Containing One O or S Atom", *Heterocyclic Compounds*, Vol. 2, John Wiley and Sons, New York, 1951, R. C. Elderfield, Ed. For a most recent review on the Synthesis and Reactions of 4-Chromanones, see: Kabbe and Widdig, *Angew Chem. Int. Ed. Engl.*, 21, 247 (1982).

The amines of Formula III in Equations 1 and 3 and the carbamates of Formula V in Equation 2 are also important intermediates for the preparation of the compounds of this invention and can be prepared by methods taught in U.S. Ser. No. 345,935.

Agriculturally suitable salts of compounds of Formula I are also useful herbicides and can be prepared in a number of ways known to the art. For example, metal salts can be made by treating compounds of Formula I with a solution of an alkali or alkaline earth metal salt having a sufficiently basic anion (e.g., hydroxide, alkoxide, carbonate or hydride). Quaternary amine salts can be made by similar techniques.

Salts of compounds of Formula I can also be prepared by exchange of one cation for another. Cationic exchange can be effected by direct treatment of an aqueous solution of a salt of a compound of Formula I (e.g., alkali metal or quaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compound of Formula I (e.g., an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

EXAMPLE 1

8-Amino-2H-1-benzothiopyran (2-Aminophenyl)allylsulfide (55 g) was heated at 250° C. for 1 hour, cooled, and then the product was distilled through a 20 cm jacketed spinning band column using a 5:1 reflux ratio. The fraction distilling at 88°–90° C. at 0.25 mmHg was collected (13.3 g) and shown to be approximately 90% pure 8-aminobenzothiopyran by NMR analysis.

90 MHz NMR (CDCl$_3$)δ: 7.0–6.3 (m, 3H, arom); 3.7 (br, 2H, NH$_2$); 3.0 (m, 2H, CH$_2$); 2.7 (m, 2H, CH$_2$); and 2.0 (m, 2H, CH$_2$).

IR (neat) 3350, 3300 and 1600 cm$^{-1}$.

EXAMPLE 2

8-Acetamido-2H-1-benzothiopyran

To a solution of 21.1 g of 8-amino-2H-1-benzothiopyran in 200 ml of 1-chlorobutane was added a solution of 13.3 ml of acetic anhydride in 50 ml of 1-chlorobutane. The temperature of the mixture rose during the addition and the mixture was refluxed for an additional 30 minutes. The solution was cooled in ice and filtered to give 18.0 g of the desired acetamide as colorless needles, m.p. 133°–135° C. The mother liquor was concentrated to ~1/5 volume to give a second crop of 4.1 g, m.p. 133°–135° C.

90 MHz NMR (CDCl$_3$)δ: 8.0–6.8 (m, 4H, arom—NH); 3.0 (m, 2H, CH$_2$); 2.8 (m, 2H, CH$_2$); and 2.1 (s and m, 5H, CH$_3$ and CH$_2$).

IR (Nujol) 3100 and 1630 cm$^{-1}$.

EXAMPLE 3

8-Acetamino-2H-1-benzothiopyran, 1,1-dioxide

To a solution of 21.0 g of 8-acetamino-2H-1-benzothiopyran in 100 ml of glacial acetic acid was added 60 ml of 30% H$_2$O$_2$ in water. The addition was accompanied by an exotherm to 70° C. and the temperature was held at 70° C. for an additional hour. The solution was cooled, diluted with water and extracted with methylene chloride. The extract was washed with water, saturated sodium bisulfite and brine, dried over MgSO$_4$ and concentrated to give 23 g of an orange oil. The oil was dissolved in 50 ml of hot 1-chlorobutane and allowed to cool to give 18.0 g of the desired dioxide as orangish-white crystals, m.p. 98°–100° C.

90 MHz NMR (CDCl$_3$)δ: 9.2 (br, 1H, NH); 8.3 (d, J=8 Hz, 1H, arom); 7.4 (t, J=8 Hz, 1H, arom); 7.0 (d, J=8 Hz, 1H, arom); 3.4 (m, 2H, CH$_2$); 3.0 (m, 2H, CH$_2$); 2.5 (m, 2H, CH$_2$); and 2.2 (s, 3H, CH$_3$).

IR (nujol) 3300 and 1690 cm$^{-1}$.

EXAMPLE 4

8-Amino-2H-1-benzothiopyran, 1,1-dioxide Hydrochloride

A solution of 17.5 g of 8-acetamino-2H-1-benzothiopyran, 1,1-dioxide in 100 ml of concentrated HCl was heated at 80°-95° C. for 1 hour, cooled in ice and filtered to give a white solid which was washed with ether and air dried to give 14.7 g of the free amine as its hydrochloride salt, m.p. 205°-209° C.

90 MHz NMR (TFA)δ: 7.9-7.5 (m, 3H, arom); 3.7 (m, 2H, CH$_2$); 3.2 (m, 2H, CH$_2$); and 2.7 (m, 2H, CH$_2$).

IR (nujol) 3200-2300 cm$^{-1}$.

EXAMPLE 5

2H-1-Benzothiopyran-8-sulfonamide, 1,1-dioxide

To a suspension of 14.0 g of 8-amino-2H-1-benzothiopyran, 1,1-dioxide hydrochloride cooled to −5° C. in 25 ml of concentrated HCl and 25 ml of glacial acetic acid was added a solution of 4.55 g of sodium nitrite in 10 ml of water at such a rate that the reaction temperature did not rise above 5° C. The mixture was stirred at 0° C. for 30 minutes then added dropwise to a solution of 50 ml of concentrated HCl, 50 ml of glacial acetic acid, 2.0 g of CuCl$_2$.2H$_2$O and 8 ml of liquified SO$_2$ cooled to −5° C. The mixture was stirred at 0° C. for 1 hour and at 20° C. for 2 hours during which time gas evolution was noted. The mixture was diluted with 400 ml of water and the resulting solid was filtered, washed with water and air dried. The solid was suspended in 250 ml of methylene chloride and contacted with 4 ml of liquified ammonia at −5° C. The suspension was stirred at room temperature for 65 hours, concentrated to a white powder, suspended in 100 ml of 1N HCl and filtered to give the sulfonamide as a white solid, 14.5 g, m.p. 214°-216° C. (wet). 13.5 g of the wet sulfonamide was suspended in xylene and refluxed under a dean-stark trap to remove water. Cooling and filtration gave 11.5 g of the sulfonamide as a white solid, m.p. 239°-241° C.

90 MHz NMR (CDCl$_3$+DMSO)δ: 8.2 (m, 1H, arom); 7.7-7.5 (m, 2H, arom); 7.1 (br, 2H, SO$_2$NH$_2$); 3.7-3.1 (m, 4H, CH$_2$'s); and 2.5 (m, CH$_2$+DMSO solvent peak).

IR (nujol) 3300, 3200, 1330 and 1170 cm$^{-1}$.

EXAMPLE 6

2H-1-Benzothiopyran-8-sulfonylisocyanate, 1,1-dioxide

A solution of 8.0 g of 2H-1-benzothiopyran-8-sulfonamide, 1,1-dioxide and 6.0 ml of n-butylisocyanate in 100 ml of 2-butanone was refluxed in the presence of 6.0 g of K$_2$CO$_3$ for 16 hours. The mixture was cooled, poured into 500 g of ice-water, acidified with 10% HCl and extracted with methylene chloride. The extract was dried over MgSO$_4$ and concentrated to give 10.2 g of the crude n-butylurea as an amber oil which solidified on standing. The crude urea was dissolved in 200 ml of dry xylenes containing 0.2 g of DABCO and 4.0 ml of n-butylisocyanate and heated to 138° C. The mixture was contacted with 4.0 ml of phosgene at such a rate that the temperature remained between 132° to 138° C. The solution was refluxed for an additional hour, cooled to 25° C., filtered under nitrogen and concentrated to give the crude sulfonylisocyanate as an oil. IR (neat) 2230 cm$^{-1}$. The crude sulfonylisocyanate was diluted to 120 ml with dry methylene chloride to give a stock solution for use in subsequent reactions.

EXAMPLE 7

N-[(4-Methoxy-6-methylpyrimidin-2-yl)aminocarbonyl]-2H-1-benzopyran-8-sulfonamide, 1,1-dioxide 0.35 g of 2-amino-4-methoxy-6-methylpyrimidine was added to 20 ml of the sulfonylisocyanate stock solution (ca. 1.3 g of the sulfonylisocyanate) prepared in Example 6 and the mixture stirred for 16 hours at 25° C. The solution was triturated with 1-chlorobutane and the crystals which formed were filtered to give 0.13 g of the desired urea, m.p. 217°-220° C.

90 MHz NMR (CDCl$_3$+DMSO)δ: 13.4 (br, 1H, NH); 9.8 (br, 1H, NH); 8.4 (m, 1H, arom); 7.8-7.5 (m, 2H, arom); 6.3 (s, 1H, CH); 4.0 (s, 3H, OCH$_3$); 3.5-3.0 (m, CH$_2$'s); 2.6-2.3 (m, CH$_2$+DMSO solvent peak); and 2.4 (s, CH$_3$).

IR (nujol) 1700 cm$^{-1}$.

Using the procedures of Examples 1-7, the following compounds may be prepared.

TABLE Ia

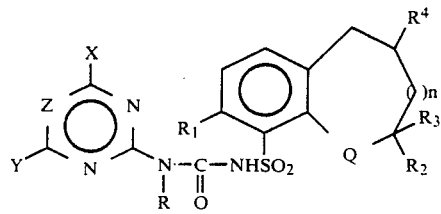

| n | Q | R | R$_1$ | R$_2$ | R$_3$ | R$_4$ | X | Y | Z | m.p.(°) |
|---|---|---|---|---|---|---|---|---|---|---|
| 0 | O | H | H | H | H | H | CH$_3$ | CH$_3$ | CH | |
| 0 | O | H | H | H | H | H | CH$_3$ | OCH$_3$ | CH | |
| 0 | O | H | H | H | H | H | OCH$_3$ | OCH$_3$ | CH | |
| 0 | O | H | H | H | H | H | CH$_3$ | CH$_3$ | N | |
| 0 | O | H | H | H | H | H | CH$_3$ | OCH$_3$ | N | |
| 0 | O | H | H | H | H | H | OCH$_3$ | OCH$_3$ | N | |
| 0 | S | H | H | H | H | H | CH$_3$ | CH$_3$ | CH | |
| 0 | S | H | H | H | H | H | CH$_3$ | OCH$_3$ | CH | |
| 0 | S | H | H | H | H | H | OCH$_3$ | OCH$_3$ | CH | |
| 0 | S | H | H | H | H | H | CH$_3$ | CH$_3$ | N | |
| 0 | S | H | H | H | H | H | CH$_3$ | OCH$_3$ | N | |
| 0 | S | H | H | H | H | H | OCH$_3$ | OCH$_3$ | N | |
| 0 | SO$_2$ | H | H | H | H | H | CH$_3$ | CH$_3$ | CH | 214-216° |

TABLE Ia-continued

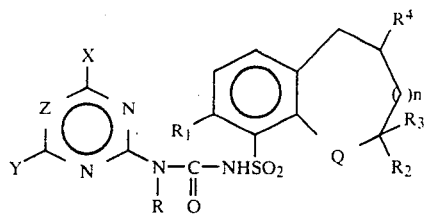

| n | Q | R | R₁ | R₂ | R₃ | R₄ | X | Y | Z | m.p.(°) |
|---|---|---|---|---|---|---|---|---|---|---|
| 0 | SO₂ | H | H | H | H | H | CH₃ | OCH₃ | CH | 217–220° |
| 0 | SO₂ | H | H | H | H | H | OCH₃ | OCH₃ | CH | 208–216° |
| 0 | SO₂ | H | H | H | H | H | CH₃ | CH₃ | N | |
| 0 | SO₂ | H | H | H | H | H | CH₃ | OCH₃ | N | 214–218° |
| 0 | SO₂ | H | H | H | H | H | OCH₃ | OCH₃ | N | |
| 0 | O | H | H | CH₃ | H | H | CH₃ | CH₃ | CH | |
| 0 | O | H | H | CH₃ | H | H | CH₃ | OCH₃ | CH | |
| 0 | O | H | H | CH₃ | H | H | OCH₃ | OCH₃ | CH | |
| 0 | O | H | H | CH₃ | H | H | CH₃ | CH₃ | N | |
| 0 | O | H | H | CH₃ | H | H | CH₃ | OCH₃ | N | |
| 0 | O | H | H | CH₃ | H | H | OCH₃ | OCH₃ | N | |
| 0 | S | H | H | CH₃ | H | H | CH₃ | CH₃ | CH | |
| 0 | S | H | H | CH₃ | H | H | CH₃ | OCH₃ | CH | |
| 0 | S | H | H | CH₃ | H | H | OCH₃ | OCH₃ | CH | |
| 0 | S | H | H | CH₃ | H | H | CH₃ | CH₃ | N | |
| 0 | S | H | H | CH₃ | H | H | CH₃ | OCH₃ | N | |
| 0 | S | H | H | CH₃ | H | H | OCH₃ | OCH₃ | N | |
| 0 | SO₂ | H | H | CH₃ | H | H | CH₃ | CH₃ | CH | |
| 0 | SO₂ | H | H | CH₃ | H | H | CH₃ | OCH₃ | CH | |
| 0 | SO₂ | H | H | CH₃ | H | H | OCH₃ | OCH₃ | CH | |
| 0 | SO₂ | H | H | CH₃ | H | H | CH₃ | CH₃ | N | |
| 0 | SO₂ | H | H | CH₃ | H | H | CH₃ | OCH₃ | N | |
| 0 | SO₂ | H | H | CH₃ | H | H | OCH₃ | OCH₃ | N | |
| 0 | O | H | H | CH₃ | CH₃ | H | CH₃ | CH₃ | CH | |
| 0 | O | H | H | CH₃ | CH₃ | H | CH₃ | OCH₃ | CH | |
| 0 | O | H | H | CH₃ | CH₃ | H | OCH₃ | OCH₃ | CH | |
| 0 | O | H | H | CH₃ | CH₃ | H | CH₃ | CH₃ | N | |
| 0 | O | H | H | CH₃ | CH₃ | H | CH₃ | OCH₃ | N | |
| 0 | O | H | H | CH₃ | CH₃ | H | OCH₃ | OCH₃ | N | |
| 0 | S | H | H | CH₃ | CH₃ | H | CH₃ | CH₃ | CH | |
| 0 | S | H | H | CH₃ | CH₃ | H | CH₃ | OCH₃ | CH | |
| 0 | S | H | H | CH₃ | CH₃ | H | OCH₃ | OCH₃ | CH | |
| 0 | S | H | H | CH₃ | CH₃ | H | CH₃ | CH₃ | N | |
| 0 | S | H | H | CH₃ | CH₃ | H | CH₃ | OCH₃ | N | |
| 0 | S | H | H | CH₃ | CH₃ | H | OCH₃ | OCH₃ | N | |
| 0 | SO₂ | H | H | CH₃ | CH₃ | H | CH₃ | CH₃ | CH | |
| 0 | SO₂ | H | H | CH₃ | CH₃ | H | CH₃ | OCH₃ | CH | |
| 0 | SO₂ | H | H | CH₃ | CH₃ | H | OCH₃ | OCH₃ | CH | |
| 0 | SO₂ | H | H | CH₃ | CH₃ | H | CH₃ | CH₃ | N | |
| 0 | SO₂ | H | H | CH₃ | CH₃ | H | CH₃ | OCH₃ | N | |
| 0 | SO₂ | H | H | CH₃ | CH₃ | H | OCH₃ | OCH₃ | N | |
| 1 | O | H | H | H | H | H | CH₃ | CH₃ | CH | |
| 1 | O | H | H | H | H | H | CH₃ | OCH₃ | CH | |
| 1 | O | H | H | H | H | H | OCH₃ | OCH₃ | CH | |
| 1 | O | H | H | H | H | H | CH₃ | CH₃ | N | |
| 1 | O | H | H | H | H | H | CH₃ | OCH₃ | N | |
| 1 | O | H | H | H | H | H | OCH₃ | OCH₃ | N | |
| 1 | S | H | H | H | H | H | CH₃ | CH₃ | CH | |
| 1 | S | H | H | H | H | H | CH₃ | OCH₃ | CH | |
| 1 | S | H | H | H | H | H | OCH₃ | OCH₃ | CH | |
| 1 | S | H | H | H | H | H | CH₃ | CH₃ | N | |
| 1 | S | H | H | H | H | H | CH₃ | OCH₃ | N | |
| 1 | S | H | H | H | H | H | OCH₃ | OCH₃ | N | |
| 1 | SO₂ | H | H | H | H | H | CH₃ | CH₃ | CH | |
| 1 | SO₂ | H | H | H | H | H | CH₃ | OCH₃ | CH | |
| 1 | SO₂ | H | H | H | H | H | OCH₃ | OCH₃ | CH | |
| 1 | SO₂ | H | H | H | H | H | CH₃ | CH₃ | N | |
| 1 | SO₂ | H | H | H | H | H | CH₃ | OCH₃ | N | |
| 1 | SO₂ | H | H | H | H | H | OCH₃ | OCH₃ | N | |
| 1 | O | H | H | CH₃ | H | H | CH₃ | CH₃ | CH | |
| 1 | O | H | H | CH₃ | H | H | CH₃ | OCH₃ | CH | |
| 1 | O | H | H | CH₃ | H | H | OCH₃ | OCH₃ | CH | |
| 1 | O | H | H | CH₃ | H | H | CH₃ | CH₃ | N | |
| 1 | O | H | H | CH₃ | H | H | CH₃ | OCH₃ | N | |
| 1 | O | H | H | CH₃ | H | H | OCH₃ | OCH₃ | N | |
| 1 | S | H | H | CH₃ | H | H | CH₃ | CH₃ | CH | |
| 1 | S | H | H | CH₃ | H | H | CH₃ | OCH₃ | CH | |
| 1 | S | H | H | CH₃ | H | H | OCH₃ | OCH₃ | CH | |
| 1 | S | H | H | CH₃ | H | H | CH₃ | CH₃ | N | |

TABLE Ia-continued

| n | Q | R | R₁ | R₂ | R₃ | R₄ | X | Y | Z | m.p.(°) |
|---|---|---|---|---|---|---|---|---|---|---|
| 1 | S | H | H | CH₃ | H | H | CH₃ | OCH₃ | N | |
| 1 | S | H | H | CH₃ | H | H | OCH₃ | OCH₃ | N | |
| 1 | SO₂ | H | H | CH₃ | H | H | CH₃ | CH₃ | CH | |
| 1 | SO₂ | H | H | CH₃ | H | H | CH₃ | OCH₃ | CH | |
| 1 | SO₂ | H | H | CH₃ | H | H | OCH₃ | OCH₃ | CH | |
| 1 | SO₂ | H | H | CH₃ | H | H | CH₃ | CH₃ | N | |
| 1 | SO₂ | H | H | CH₃ | H | H | CH₃ | OCH₃ | N | |
| 1 | SO₂ | H | H | CH₃ | H | H | OCH₃ | OCH₃ | N | |
| 1 | O | H | H | CH₃ | CH₃ | H | CH₃ | CH₃ | CH | |
| 1 | O | H | H | CH₃ | CH₃ | H | CH₃ | OCH₃ | CH | |
| 1 | O | H | H | CH₃ | CH₃ | H | OCH₃ | OCH₃ | CH | |
| 1 | O | H | H | CH₃ | CH₃ | H | CH₃ | CH₃ | N | |
| 1 | O | H | H | CH₃ | CH₃ | H | CH₃ | OCH₃ | N | |
| 1 | O | H | H | CH₃ | CH₃ | H | OCH₃ | OCH₃ | N | |
| 1 | S | H | H | CH₃ | CH₃ | H | CH₃ | CH₃ | CH | |
| 1 | S | H | H | CH₃ | CH₃ | H | CH₃ | OCH₃ | CH | |
| 1 | S | H | H | CH₃ | CH₃ | H | OCH₃ | OCH₃ | CH | |
| 1 | S | H | H | CH₃ | CH₃ | H | CH₃ | CH₃ | N | |
| 1 | S | H | H | CH₃ | CH₃ | H | CH₃ | OCH₃ | N | |
| 1 | S | H | H | CH₃ | CH₃ | H | OCH₃ | OCH₃ | N | |
| 1 | SO₂ | H | H | CH₃ | CH₃ | H | CH₃ | CH₃ | CH | |
| 1 | SO₂ | H | H | CH₃ | CH₃ | H | CH₃ | OCH₃ | CH | |
| 1 | SO₂ | H | H | CH₃ | CH₃ | H | OCH₃ | OCH₃ | CH | |
| 1 | SO₂ | H | H | CH₃ | CH₃ | H | CH₃ | CH₃ | N | |
| 1 | SO₂ | H | H | CH₃ | CH₃ | H | CH₃ | OCH₃ | N | |
| 1 | SO₂ | H | H | CH₃ | CH₃ | H | OCH₃ | OCH₃ | N | |
| 0 | SO₂ | CH₃ | H | CH₃ | H | H | OCH₃ | OCH₃ | N | |
| 0 | SO₂ | H | H | H | H | CH₃ | CH₃ | CH₃ | CH | |
| 0 | SO₂ | H | H | H | H | CH₃ | CH₃ | OCH₃ | CH | 243–245° |
| 0 | SO₂ | H | H | H | H | CH₃ | OCH₃ | OCH₃ | CH | 244–245° |
| 0 | SO₂ | H | H | H | H | CH₃ | CH₃ | CH₃ | N | |
| 0 | SO₂ | H | H | H | H | CH₃ | CH₃ | OCH₃ | N | 206–209° |
| 0 | SO₂ | H | H | H | H | CH₃ | OCH₃ | OCH₃ | N | 228–230° |
| 0 | O | H | OCH₃ | CH₃ | CH₃ | H | CH₃ | CH₃ | CH | |
| 0 | O | H | OCH₃ | CH₃ | CH₃ | H | CH₃ | OCH₃ | CH | |
| 0 | O | H | OCH₃ | CH₃ | CH₃ | H | OCH₃ | OCH₃ | CH | |
| 0 | O | H | OCH₃ | CH₃ | CH₃ | H | CH₃ | CH₃ | N | |
| 0 | O | H | OCH₃ | CH₃ | CH₃ | H | CH₃ | OCH₃ | N | |
| 0 | O | H | OCH₃ | CH₃ | CH₃ | H | OCH₃ | OCH₃ | N | |
| 0 | O | H | CH₃ | H | H | H | OCH₃ | OCH₃ | CH | |
| 0 | S | H | Cl | CH₃ | H | H | OCH₃ | OCH₃ | CH | |
| 0 | SO₂ | H | Br | H | CH₃ | H | OCH₃ | OCH₃ | CH | |
| 0 | O | H | CO₂CH₃ | CH₃ | H | H | CH₃ | OCH₃ | CH | |
| 0 | S | H | CO₂CH₂CH₃ | H | CH₃ | H | OCH₃ | OCH₃ | CH | |
| 0 | SO₂ | H | CO₂CH₂CH₂CH₃ | CH₃ | H | H | CH₃ | OCH₃ | N | |
| 0 | O | H | CO₂CH(CH₃)₂ | H | CH₃ | H | OCH₃ | OCH₃ | N | |
| 0 | S | H | CO₂CH₂CH=CH₂ | CH₃ | H | H | CH₃ | OCH₃ | CH | |
| 0 | SO₂ | H | CO₂CH₂CH₂OCH₃ | H | CH₃ | H | OCH₃ | OCH₃ | CH | |
| 0 | O | H | CO₂CH₂CH₂Cl | CH₃ | H | H | CH₃ | OCH₃ | N | |
| 0 | S | H | SO₂CH₃ | H | CH₃ | H | OCH₃ | OCH₃ | N | |
| 0 | SO₂ | H | SO₂CH₂CH₂CH₃ | CH₃ | H | H | CH₃ | OCH₃ | CH | |
| 0 | O | H | SO₂CH(CH₃)₂ | H | CH₃ | H | OCH₃ | OCH₃ | CH | |
| 0 | S | H | OSO₂CH₃ | CH₃ | H | H | CH₃ | OCH₃ | N | |
| 0 | SO₂ | H | OSO₂CF₃ | H | CH₃ | H | OCH₃ | OCH₃ | N | |
| 0 | O | H | OSO₂CH(CH₃)₂ | H | CH₃ | H | CH₃ | OCH₃ | CH | |
| 0 | SO₂ | H | SO₂N(CH₃)₂ | CH₃ | H | H | OCH₃ | OCH₃ | CH | |
| 0 | SO₂ | H | SO₂N(CH₂CH₃)₂ | H | CH₃ | H | CH₃ | OCH₃ | N | |
| 0 | O | H | SO₂N(CH₃)CH₂CH₃ | CH₃ | H | H | OCH₃ | OCH₃ | N | |
| 0 | S | H | H | CH₃ | CH₂CH₃ | H | CH₃ | OCH₃ | CH | |
| 0 | SO₂ | H | H | H | CH₂CH₂CH₃ | H | OCH₃ | OCH₃ | CH | |
| 0 | O | H | H | H | CH(CH₃)₂ | H | CH₃ | OCH₃ | N | |
| 0 | S | H | H | CH₂CH₃ | H | H | OCH₃ | OCH₃ | N | |
| 0 | SO₂ | H | H | CH₂CH₂CH₃ | H | H | CH₃ | OCH₃ | CH | |
| 0 | O | H | H | CH(CH₃)₂ | H | H | OCH₃ | OCH₃ | CH | |
| 0 | S | H | H | H | CH₃ | H | Cl | OCH₃ | CH | |
| 0 | SO₂ | H | H | H | CH₃ | H | CH₃ | NH₂ | CH | |
| 0 | O | H | H | H | CH₃ | H | CH₃ | NHCH₃ | CH | |
| 0 | S | H | H | H | CH₃ | H | CH₃ | N(CH₃)₂ | CH | |
| 0 | SO₂ | H | H | H | CH₃ | H | CH₃ | OC₂H₅ | CH | |
| 0 | O | H | H | CH₃ | H | H | CH₃ | OCH₂CH₃ | N | |

TABLE Ia-continued

| n | Q | R | R₁ | R₂ | R₃ | R₄ | X | Y | Z | m.p.(°) |
|---|---|---|----|----|----|----|---|---|---|---------|
| 0 | S | H | H | H | CH₃ | H | OCH₃ | CH₂OCH₃ | CH | |

TABLE Ib

| n | Q | R | R₁ | R₂ | R₃ | R₄ | X' | G |
|---|---|---|----|----|----|----|----|---|
| 0 | SO₂ | H | H | H | H | H | CH₃ | CH₂ |
| 0 | SO₂ | H | H | H | H | H | OCH₃ | CH₂ |
| 0 | SO₂ | H | H | H | H | H | OCH₂CH₃ | CH₂ |
| 0 | SO₂ | H | H | H | H | H | CH₃ | O |
| 0 | SO₂ | H | H | H | H | H | OCH₃ | O |
| 0 | SO₂ | H | H | H | H | H | OCH₂CH₃ | O |
| 0 | SO₂ | H | H | H | H | CH₃ | OCH₃ | O |
| 0 | O | H | H | H | CH₃ | H | OCH₃ | O |
| 0 | S | H | H | CH₃ | H | H | OCH₃ | O |
| 0 | SO₂ | H | H | H | CH₃ | H | OCH₃ | O |
| 0 | S | H | CH₃ | CH₃ | H | H | OCH₃ | O |
| 0 | SO₂ | H | OCH₃ | CH₃ | H | H | OCH₃ | O |
| 0 | S | H | Cl | CH₃ | H | H | OCH₃ | O |
| 0 | SO₂ | H | Br | CH₃ | H | H | OCH₃ | O |
| 0 | S | H | CO₂CH₃ | CH₃ | H | H | OCH₃ | O |
| 0 | SO₂ | H | SO₂CH₃ | CH₃ | H | H | OCH₃ | O |
| 0 | S | H | OSO₂CH₃ | CH₃ | H | H | OCH₃ | O |
| 0 | SO₂ | H | SO₂N(CH₃)₂ | CH₃ | H | H | OCH₃ | O |
| 1 | SO₂ | H | H | H | H | H | OCH₃ | O |

TABLE Ic

| n | Q | R | R₁ | R₂ | R₃ | R₄ | X' |
|---|---|---|----|----|----|----|----|
| 0 | SO₂ | H | H | H | H | H | CH₃ |
| 0 | SO₂ | H | H | H | H | H | OCH₃ |
| 0 | SO₂ | H | H | H | H | H | OCH₂CH₃ |
| 0 | SO₂ | H | H | H | H | CH₃ | OCH₃ |
| 0 | O | H | H | H | CH₃ | H | OCH₃ |
| 0 | S | H | H | CH₃ | H | H | OCH₃ |
| 0 | SO₂ | H | H | H | CH₃ | H | OCH₃ |

TABLE Ic-continued

| n | Q | R | R₁ | R₂ | R₃ | R₄ | X' |
|---|---|---|----|----|----|----|----|
| 0 | S | H | CH₃ | CH₃ | H | H | OCH₃ |
| 0 | SO₂ | H | OCH₃ | CH₃ | H | H | OCH₃ |
| 0 | S | H | Cl | CH₃ | H | H | OCH₃ |
| 0 | SO₂ | H | Br | CH₃ | H | H | OCH₃ |
| 0 | S | H | CO₂CH₃ | CH₃ | H | H | OCH₃ |
| 0 | SO₂ | H | SO₂CH₃ | CH₃ | H | H | OCH₃ |
| 0 | S | H | OSO₂CH₃ | CH₃ | H | H | OCH₃ |
| 0 | SO₂ | H | SO₂N(CH₃)₂ | CH₃ | H | H | OCH₃ |
| 1 | SO₂ | H | H | H | H | H | OCH₃ |

TABLE Id

| n | Q | R | R₁ | R₂ | R₃ | R₄ | X' |
|---|---|---|----|----|----|----|----|
| 0 | SO₂ | H | H | H | H | H | CH₃ |
| 0 | SO₂ | H | H | H | H | H | OCH₃ |
| 0 | SO₂ | H | H | H | H | H | OCH₂CH₃ |
| 0 | SO₂ | H | H | H | H | CH₃ | OCH₃ |
| 0 | O | H | H | H | CH₃ | H | OCH₃ |
| 0 | S | H | H | CH₃ | H | H | OCH₃ |
| 0 | SO₂ | H | H | H | CH₃ | H | OCH₃ |
| 0 | S | H | CH₃ | CH₃ | H | H | OCH₃ |
| 0 | SO₂ | H | OCH₃ | CH₃ | H | H | OCH₃ |
| 0 | S | H | Cl | CH₃ | H | H | OCH₃ |
| 0 | SO₂ | H | Br | CH₃ | H | H | OCH₃ |
| 0 | S | H | CO₂CH₃ | CH₃ | H | H | OCH₃ |
| 0 | SO₂ | H | SO₂CH₃ | CH₃ | H | H | OCH₃ |
| 0 | S | H | OSO₂CH₃ | CH₃ | H | H | OCH₃ |
| 0 | SO₂ | H | SO₂N(CH₃)₂ | CH₃ | H | H | OCH₃ |
| 1 | SO₂ | H | H | H | H | H | OCH₃ |

TABLE IIa

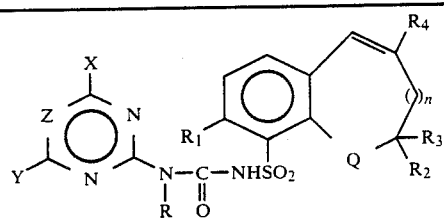

| n | Q | R | R₁ | R₂ | R₃ | R₄ | X | Y | Z | m.p. (°) |
|---|---|---|----|----|----|----|---|---|---|----------|
| 0 | O | H | H | H | H | H | CH₃ | CH₃ | CH | |
| 0 | O | H | H | H | H | H | CH₃ | OCH₃ | CH | |
| 0 | O | H | H | H | H | H | OCH₃ | OCH₃ | CH | |
| 0 | O | H | H | H | H | H | CH₃ | CH₃ | N | |
| 0 | O | H | H | H | H | H | CH₃ | OCH₃ | N | |
| 0 | O | H | H | H | H | H | OCH₃ | OCH₃ | N | |
| 0 | S | H | H | H | H | H | CH₃ | CH₃ | CH | |
| 0 | S | H | H | H | H | H | CH₃ | OCH₃ | CH | |
| 0 | S | H | H | H | H | H | OCH₃ | OCH₃ | CH | |
| 0 | S | H | H | H | H | H | CH₃ | CH₃ | N | |
| 0 | S | H | H | H | H | H | CH₃ | OCH₃ | N | |
| 0 | S | H | H | H | H | H | OCH₃ | OCH₃ | N | |
| 0 | SO₂ | H | H | H | H | H | CH₃ | CH₃ | CH | |
| 0 | SO₂ | H | H | H | H | H | CH₃ | OCH₃ | CH | |
| 0 | SO₂ | H | H | H | H | H | OCH₃ | OCH₃ | CH | |
| 0 | SO₂ | H | H | H | H | H | CH₃ | CH₃ | N | |
| 0 | SO₂ | H | H | H | H | H | CH₃ | OCH₃ | N | |
| 0 | SO₂ | H | H | H | H | H | OCH₃ | OCH₃ | N | |
| 0 | O | H | H | CH₃ | H | H | CH₃ | CH₃ | CH | |
| 0 | O | H | H | CH₃ | H | H | CH₃ | OCH₃ | CH | |
| 0 | O | H | H | CH₃ | H | H | OCH₃ | OCH₃ | CH | |
| 0 | O | H | H | CH₃ | H | H | CH₃ | CH₃ | N | |
| 0 | O | H | H | CH₃ | H | H | CH₃ | OCH₃ | N | |
| 0 | O | H | H | CH₃ | H | H | OCH₃ | OCH₃ | N | |
| 0 | S | H | H | CH₃ | H | H | CH₃ | CH₃ | CH | |
| 0 | S | H | H | CH₃ | H | H | CH₃ | OCH₃ | CH | |
| 0 | S | H | H | CH₃ | H | H | OCH₃ | OCH₃ | CH | |
| 0 | S | H | H | CH₃ | H | H | CH₃ | CH₃ | N | |
| 0 | S | H | H | CH₃ | H | H | CH₃ | OCH₃ | N | |
| 0 | S | H | H | CH₃ | H | H | OCH₃ | OCH₃ | N | |
| 0 | SO₂ | H | H | CH₃ | H | H | CH₃ | CH₃ | CH | |
| 0 | SO₂ | H | H | CH₃ | H | H | CH₃ | OCH₃ | CH | |
| 0 | SO₂ | H | H | CH₃ | H | H | OCH₃ | OCH₃ | CH | |
| 0 | SO₂ | H | H | CH₃ | H | H | CH₃ | CH₃ | N | |
| 0 | SO₂ | H | H | CH₃ | H | H | CH₃ | OCH₃ | N | |
| 0 | SO₂ | H | H | CH₃ | H | H | OCH₃ | OCH₃ | N | |
| 0 | O | H | H | CH₃ | CH₃ | H | CH₃ | CH₃ | CH | |
| 0 | O | H | H | CH₃ | CH₃ | H | CH₃ | OCH₃ | CH | |
| 0 | O | H | H | CH₃ | CH₃ | H | OCH₃ | OCH₃ | CH | |
| 0 | O | H | H | CH₃ | CH₃ | H | CH₃ | CH₃ | N | |
| 0 | O | H | H | CH₃ | CH₃ | H | CH₃ | OCH₃ | N | |
| 0 | O | H | H | CH₃ | CH₃ | H | OCH₃ | OCH₃ | N | |
| 0 | S | H | H | CH₃ | CH₃ | H | CH₃ | CH₃ | CH | |
| 0 | S | H | H | CH₃ | CH₃ | H | CH₃ | OCH₃ | CH | |
| 0 | S | H | H | CH₃ | CH₃ | H | OCH₃ | OCH₃ | CH | |
| 0 | S | H | H | CH₃ | CH₃ | H | CH₃ | CH₃ | N | |
| 0 | S | H | H | CH₃ | CH₃ | H | CH₃ | OCH₃ | N | |
| 0 | S | H | H | CH₃ | CH₃ | H | OCH₃ | OCH₃ | N | |
| 0 | SO₂ | H | H | CH₃ | CH₃ | H | CH₃ | CH₃ | CH | |
| 0 | SO₂ | H | H | CH₃ | CH₃ | H | CH₃ | OCH₃ | CH | |
| 0 | SO₂ | H | H | CH₃ | CH₃ | H | OCH₃ | OCH₃ | CH | |
| 0 | SO₂ | H | H | CH₃ | CH₃ | H | CH₃ | CH₃ | N | |
| 0 | SO₂ | H | H | CH₃ | CH₃ | H | CH₃ | OCH₃ | N | |
| 0 | SO₂ | H | H | CH₃ | CH₃ | H | OCH₃ | OCH₃ | N | |
| 1 | O | H | H | H | H | H | CH₃ | CH₃ | CH | |
| 1 | O | H | H | H | H | H | CH₃ | OCH₃ | CH | |
| 1 | O | H | H | H | H | H | OCH₃ | OCH₃ | CH | |
| 1 | O | H | H | H | H | H | CH₃ | CH₃ | N | |
| 1 | O | H | H | H | H | H | CH₃ | OCH₃ | N | |
| 1 | O | H | H | H | H | H | OCH₃ | OCH₃ | N | |
| 1 | S | H | H | H | H | H | CH₃ | CH₃ | CH | |
| 1 | S | H | H | H | H | H | CH₃ | OCH₃ | CH | |
| 1 | S | H | H | H | H | H | OCH₃ | OCH₃ | CH | |
| 1 | S | H | H | H | H | H | CH₃ | CH₃ | N | |
| 1 | S | H | H | H | H | H | CH₃ | OCH₃ | N | |
| 1 | S | H | H | H | H | H | OCH₃ | OCH₃ | N | |
| 1 | SO₂ | H | H | H | H | H | CH₃ | CH₃ | CH | |
| 1 | SO₂ | H | H | H | H | H | CH₃ | OCH₃ | CH | |
| 1 | SO₂ | H | H | H | H | H | OCH₃ | OCH₃ | CH | |
| 1 | SO₂ | H | H | H | H | H | CH₃ | CH₃ | N | |

TABLE IIa-continued

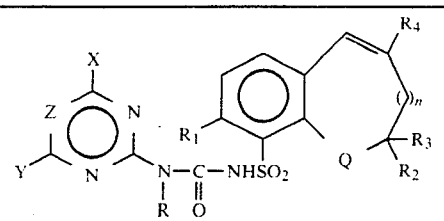

| n | Q | R | $R_1$ | $R_2$ | $R_3$ | $R_4$ | X | Y | Z | m.p. (°) |
|---|---|---|---|---|---|---|---|---|---|---|
| 1 | $SO_2$ | H | H | H | H | H | $CH_3$ | $OCH_3$ | N | |
| 1 | $SO_2$ | H | H | H | H | H | $OCH_3$ | $OCH_3$ | N | |
| 1 | O | H | H | $CH_3$ | H | H | $CH_3$ | $CH_3$ | CH | |
| 1 | O | H | H | $CH_3$ | H | H | $CH_3$ | $OCH_3$ | CH | |
| 1 | O | H | H | $CH_3$ | H | H | $OCH_3$ | $OCH_3$ | CH | |
| 1 | O | H | H | $CH_3$ | H | H | $CH_3$ | $CH_3$ | N | |
| 1 | O | H | H | $CH_3$ | H | H | $CH_3$ | $OCH_3$ | N | |
| 1 | O | H | H | $CH_3$ | H | H | $OCH_3$ | $OCH_3$ | N | |
| 1 | S | H | H | $CH_3$ | H | H | $CH_3$ | $CH_3$ | CH | |
| 1 | S | H | H | $CH_3$ | H | H | $CH_3$ | $OCH_3$ | CH | |
| 1 | S | H | H | $CH_3$ | H | H | $OCH_3$ | $OCH_3$ | CH | |
| 1 | S | H | H | $CH_3$ | H | H | $CH_3$ | $CH_3$ | N | |
| 1 | S | H | H | $CH_3$ | H | H | $CH_3$ | $OCH_3$ | N | |
| 1 | S | H | H | $CH_3$ | H | H | $OCH_3$ | $OCH_3$ | N | |
| 1 | $SO_2$ | H | H | $CH_3$ | H | H | $CH_3$ | $CH_3$ | CH | |
| 1 | $SO_2$ | H | H | $CH_3$ | H | H | $CH_3$ | $OCH_3$ | CH | |
| 1 | $SO_2$ | H | H | $CH_3$ | H | H | $OCH_3$ | $OCH_3$ | CH | |
| 1 | $SO_2$ | H | H | $CH_3$ | H | H | $CH_3$ | $CH_3$ | N | |
| 1 | $SO_2$ | H | H | $CH_3$ | H | H | $CH_3$ | $OCH_3$ | N | |
| 1 | $SO_2$ | H | H | $CH_3$ | H | H | $OCH_3$ | $OCH_3$ | N | |
| 1 | O | H | H | $CH_3$ | $CH_3$ | H | $CH_3$ | $CH_3$ | CH | |
| 1 | O | H | H | $CH_3$ | $CH_3$ | H | $CH_3$ | $OCH_3$ | CH | |
| 1 | O | H | H | $CH_3$ | $CH_3$ | H | $OCH_3$ | $OCH_3$ | CH | |
| 1 | O | H | H | $CH_3$ | $CH_3$ | H | $CH_3$ | $CH_3$ | N | |
| 1 | O | H | H | $CH_3$ | $CH_3$ | H | $CH_3$ | $OCH_3$ | N | |
| 1 | O | H | H | $CH_3$ | $CH_3$ | H | $OCH_3$ | $OCH_3$ | N | |
| 1 | S | H | H | $CH_3$ | $CH_3$ | H | $CH_3$ | $CH_3$ | CH | |
| 1 | S | H | H | $CH_3$ | $CH_3$ | H | $CH_3$ | $OCH_3$ | CH | |
| 1 | S | H | H | $CH_3$ | $CH_3$ | H | $OCH_3$ | $OCH_3$ | CH | |
| 1 | S | H | H | $CH_3$ | $CH_3$ | H | $CH_3$ | $CH_3$ | N | |
| 1 | S | H | H | $CH_3$ | $CH_3$ | H | $CH_3$ | $OCH_3$ | N | |
| 1 | S | H | H | $CH_3$ | $CH_3$ | H | $OCH_3$ | $OCH_3$ | N | |
| 1 | $SO_2$ | H | H | $CH_3$ | $CH_3$ | H | $CH_3$ | $CH_3$ | CH | |
| 1 | $SO_2$ | H | H | $CH_3$ | $CH_3$ | H | $CH_3$ | $OCH_3$ | CH | |
| 1 | $SO_2$ | H | H | $CH_3$ | $CH_3$ | H | $OCH_3$ | $OCH_3$ | CH | |
| 1 | $SO_2$ | H | H | $CH_3$ | $CH_3$ | H | $CH_3$ | $CH_3$ | N | |
| 1 | $SO_2$ | H | H | $CH_3$ | $CH_3$ | H | $CH_3$ | $OCH_3$ | N | |
| 1 | $SO_2$ | H | H | $CH_3$ | $CH_3$ | H | $OCH_3$ | $OCH_3$ | N | |
| 0 | $SO_2$ | $CH_3$ | H | $CH_3$ | H | H | $OCH_3$ | $OCH_3$ | N | |
| 0 | $SO_2$ | H | H | H | H | H | $CH_3$ | $CH_3$ | CH | |
| 0 | $SO_2$ | H | H | H | H | H | $CH_3$ | $OCH_3$ | CH | |
| 0 | $SO_2$ | H | H | H | H | H | $CH_3$ | $OCH_3$ | CH | |
| 0 | $SO_2$ | H | H | H | H | H | $CH_3$ | $CH_3$ | N | |
| 0 | $SO_2$ | H | H | H | H | H | $CH_3$ | $OCH_3$ | N | |
| 0 | $SO_2$ | H | H | H | H | H | $CH_3$ | $OCH_3$ | N | |
| 0 | O | H | $OCH_3$ | $CH_3$ | $CH_3$ | H | $CH_3$ | $CH_3$ | CH | |
| 0 | O | H | $OCH_3$ | $CH_3$ | $CH_3$ | H | $CH_3$ | $OCH_3$ | CH | |
| 0 | O | H | $OCH_3$ | $CH_3$ | $CH_3$ | H | $OCH_3$ | $OCH_3$ | CH | |
| 0 | O | H | $OCH_3$ | $CH_3$ | $CH_3$ | H | $CH_3$ | $CH_3$ | N | |
| 0 | O | H | $OCH_3$ | $CH_3$ | $CH_3$ | H | $CH_3$ | $OCH_3$ | N | |
| 0 | O | H | $CH_3$ | $CH_3$ | H | $OCH_3$ | $OCH_3$ | N | | |
| 0 | O | H | $CH_3$ | H | H | H | $OCH_3$ | $OCH_3$ | CH | |
| 0 | S | H | Cl | $CH_3$ | H | H | $OCH_3$ | $OCH_3$ | CH | |
| 0 | $SO_2$ | H | Br | H | $CH_3$ | H | $OCH_3$ | $OCH_3$ | CH | |
| 0 | O | H | $CO_2CH_3$ | $CH_3$ | H | H | $OCH_3$ | $OCH_3$ | CH | |
| 0 | S | H | $CO_2CH_2CH_3$ | H | $CH_3$ | H | $CH_3$ | $OCH_3$ | CH | |
| 0 | $SO_2$ | H | $CO_2CH_2CH_2CH_3$ | $CH_3$ | H | H | $CH_3$ | $OCH_3$ | N | |
| 0 | O | H | $CO_2CH(CH_3)_2$ | H | $CH_3$ | H | $CH_3$ | $OCH_3$ | N | |
| 0 | S | H | $CO_2CH_2CH=CH_2$ | $CH_3$ | H | H | $CH_3$ | $OCH_3$ | CH | |
| 0 | $SO_2$ | H | $CO_2CH_2CH_2OCH_3$ | H | $CH_3$ | H | $CH_3$ | $OCH_3$ | CH | |
| 0 | O | H | $CO_2CH_2CH_2Cl$ | $CH_3$ | H | H | $CH_3$ | $OCH_3$ | N | |
| 0 | S | H | $SO_2CH_3$ | H | $CH_3$ | H | $CH_3$ | $OCH_3$ | N | |
| 0 | $SO_2$ | H | $SO_2CH_2CH_2CH_3$ | $CH_3$ | H | H | $CH_3$ | $OCH_3$ | CH | |
| 0 | O | H | $SO_2CH(CH_3)_2$ | H | $CH_3$ | H | $CH_3$ | $OCH_3$ | CH | |
| 0 | S | H | $OSO_2CH_3$ | $CH_3$ | H | H | $CH_3$ | $OCH_3$ | N | |
| 0 | $SO_2$ | H | $OSO_2CF_3$ | H | $CH_3$ | H | $CH_3$ | $OCH_3$ | N | |
| 0 | O | H | $OSO_2CH(CH_3)_2$ | H | H | H | $CH_3$ | $OCH_3$ | CH | |
| 0 | $SO_2$ | H | $SO_2N(CH_3)_2$ | $CH_3$ | H | H | $CH_3$ | $OCH_3$ | CH | |
| 0 | $SO_2$ | H | $SO_2N(CH_2CH_3)_2$ | H | $CH_3$ | H | $CH_3$ | $OCH_3$ | N | |
| 0 | O | H | $SO_2N(CH_3)CH_2CH_3$ | $CH_3$ | H | H | $OCH_3$ | $OCH_3$ | N | |

TABLE IIa-continued

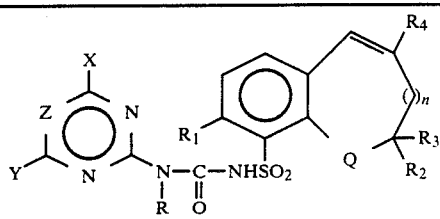

| n | Q | R | $R_1$ | $R_2$ | $R_3$ | $R_4$ | X | Y | Z | m.p. (°) |
|---|---|---|---|---|---|---|---|---|---|---|
| 0 | S | H | H | $CH_3$ | $CH_2CH_3$ | H | $CH_3$ | $OCH_3$ | CH | |
| 0 | $SO_2$ | H | H | H | $CH_2CH_2CH_3$ | H | $OCH_3$ | $OCH_3$ | CH | |
| 0 | O | H | H | H | $CH(CH_3)_2$ | H | $CH_3$ | $OCH_3$ | N | |
| 0 | S | H | H | $CH_2CH_3$ | H | H | $OCH_3$ | $OCH_3$ | N | |
| 0 | $SO_2$ | H | H | $CH_2CH_2CH_3$ | H | H | $CH_3$ | $OCH_3$ | CH | |
| 0 | O | H | H | $CH(CH_3)_2$ | H | H | $OCH_3$ | $OCH_3$ | CH | |
| 0 | S | H | H | H | Cl | $CH_3$ | H | $CH_3$ | $OCH_3$ | CH |
| 0 | $SO_2$ | H | H | $CH_3$ | H | H | $CH_3$ | $NH_2$ | CH | |
| 0 | O | H | H | H | $CH_3$ | H | $CH_3$ | $NHCH_3$ | CH | |
| 0 | S | H | H | $CH_3$ | H | H | $CH_3$ | $N(CH_3)_2$ | CH | |
| 0 | $SO_2$ | H | H | H | $CH_3$ | H | $CH_3$ | $OC_2H_5$ | CH | |
| 0 | O | H | H | $CH_3$ | H | H | $CH_3$ | $OCH_2CH_3$ | N | |
| 0 | S | H | H | H | $CH_3$ | H | $OCH_3$ | $CH_2OCH_3$ | CH | |

TABLE IIb

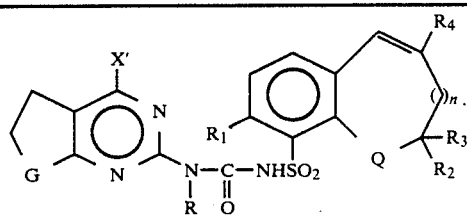

| n | Q | R | $R_1$ | $R_2$ | $R_3$ | $R_4$ | X' | G |
|---|---|---|---|---|---|---|---|---|
| 0 | $SO_2$ | H | H | H | H | H | $CH_3$ | $CH_2$ |
| 0 | $SO_2$ | H | H | H | H | H | $OCH_3$ | $CH_2$ |
| 0 | $SO_2$ | H | H | H | H | H | $OCH_2CH_3$ | $CH_2$ |
| 0 | $SO_2$ | H | H | H | H | $CH_3$ | $OCH_3$ | $CH_2$ |
| 0 | $SO_2$ | H | H | H | H | H | $CH_3$ | O |
| 0 | $SO_2$ | H | H | H | H | H | $OCH_3$ | O |
| 0 | $SO_2$ | H | H | H | H | H | $OCH_2CH_3$ | O |
| 0 | $SO_2$ | H | H | H | H | $CH_3$ | $OCH_3$ | O |
| 0 | O | H | H | H | $CH_3$ | H | $OCH_3$ | O |
| 0 | S | H | H | $CH_3$ | H | H | $OCH_3$ | O |
| 0 | $SO_2$ | H | H | H | $CH_3$ | H | $OCH_3$ | O |
| 0 | S | H | $CH_3$ | $CH_3$ | H | H | $OCH_3$ | O |
| 0 | $SO_2$ | H | $OCH_3$ | $CH_3$ | H | H | $OCH_3$ | O |
| 0 | S | H | Cl | $CH_3$ | H | H | $OCH_3$ | O |
| 0 | $SO_2$ | H | Br | $CH_3$ | H | H | $OCH_3$ | O |
| 0 | S | H | $CO_2CH_3$ | $CH_3$ | H | H | $OCH_3$ | O |
| 0 | $SO_2$ | H | $SO_2CH_3$ | $CH_3$ | H | H | $OCH_3$ | O |
| 0 | S | H | $OSO_2CH_3$ | $CH_3$ | H | H | $OCH_3$ | O |
| 0 | $SO_2$ | H | $SO_2N(CH_3)_2$ | $CH_3$ | H | H | $OCH_3$ | O |
| 1 | $SO_2$ | H | H | H | H | H | $OCH_3$ | O |

TABLE IIc

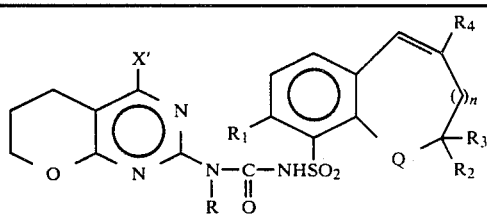

| n | Q | R | $R_1$ | $R_2$ | $R_3$ | $R_4$ | X' |
|---|---|---|---|---|---|---|---|
| 0 | $SO_2$ | H | H | H | H | H | $CH_3$ |
| 0 | $SO_2$ | H | H | H | H | H | $OCH_3$ |
| 0 | $SO_2$ | H | H | H | H | H | $OCH_2CH_3$ |
| 0 | $SO_2$ | H | H | H | H | $CH_3$ | $OCH_3$ |
| 0 | O | H | H | H | $CH_3$ | H | $OCH_3$ |

TABLE IIc-continued

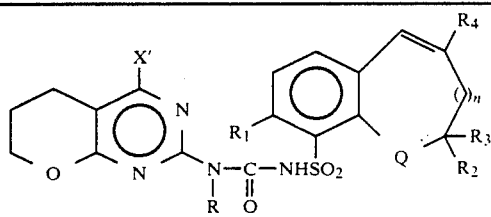

| n | Q | R | $R_1$ | $R_2$ | $R_3$ | $R_4$ | X' |
|---|---|---|---|---|---|---|---|
| 0 | S | H | H | $CH_3$ | H | H | $OCH_3$ |
| 0 | $SO_2$ | H | H | H | $CH_3$ | H | $OCH_3$ |
| 0 | S | H | $CH_3$ | $CH_3$ | H | H | $OCH_3$ |
| 0 | $SO_2$ | H | $OCH_3$ | $CH_3$ | H | H | $OCH_3$ |
| 0 | S | H | Cl | $CH_3$ | H | H | $OCH_3$ |
| 0 | $SO_2$ | H | Br | $CH_3$ | H | H | $OCH_3$ |
| 0 | S | H | $CO_2CH_3$ | $CH_3$ | H | H | $OCH_3$ |
| 0 | $SO_2$ | H | $SO_2CH_3$ | $CH_3$ | H | H | $OCH_3$ |
| 0 | S | H | $OSO_2CH_3$ | $CH_3$ | H | H | $OCH_3$ |
| 0 | $SO_2$ | H | $SO_2N(CH_3)_2$ | $CH_3$ | H | H | $OCH_3$ |
| 1 | $SO_2$ | H | H | H | H | H | $OCH_3$ |

TABLE IId

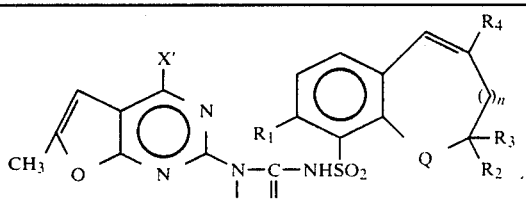

| n | Q | R | $R_1$ | $R_2$ | $R_3$ | $R_4$ | X' |
|---|---|---|---|---|---|---|---|
| 0 | $SO_2$ | H | H | H | H | H | $CH_3$ |
| 0 | $SO_2$ | H | H | H | H | H | $OCH_3$ |
| 0 | $SO_2$ | H | H | H | H | H | $OCH_2CH_3$ |
| 0 | $SO_2$ | H | H | H | H | $CH_3$ | $OCH_3$ |
| 0 | O | H | H | H | $CH_3$ | H | $OCH_3$ |
| 0 | S | H | H | $CH_3$ | H | H | $OCH_3$ |
| 0 | $SO_2$ | H | H | H | $CH_3$ | H | $OCH_3$ |
| 0 | S | H | $CH_3$ | $CH_3$ | H | H | $OCH_3$ |
| 0 | $SO_2$ | H | $OCH_3$ | $CH_3$ | H | H | $OCH_3$ |
| 0 | S | H | Cl | $CH_3$ | H | H | $OCH_3$ |
| 0 | $SO_2$ | H | Br | $CH_3$ | H | H | $OCH_3$ |
| 0 | S | H | $CO_2CH_3$ | $CH_3$ | H | H | $OCH_3$ |
| 0 | $SO_2$ | H | $SO_2CH_3$ | $CH_3$ | H | H | $OCH_3$ |

TABLE IId-continued

Structure with substituents: R, R₁, R₂, R₃, R₄, X', Q, n

| n | Q | R | R₁ | R₂ | R₃ | R₄ | X' |
|---|---|---|---|---|---|---|---|
| 0 | S | H | OSO₂CH₃ | CH₃ | H | H | OCH₃ |
| 0 | SO₂ | H | SO₂N(CH₃)₂ | CH₃ | H | H | OCH₃ |
| 1 | SO₂ | H | H | H | H | H | OCH₃ |

TABLE IIIa

| n | Q | R | R₁ | R₂ | R₄ | X | Y | Z | m.p.(°) |
|---|---|---|---|---|---|---|---|---|---|
| 0 | S | H | H | H | H | CH₃ | CH₃ | CH | |
| 0 | S | H | H | H | H | CH₃ | OCH₃ | CH | |
| 0 | S | H | H | H | H | OCH₃ | OCH₃ | CH | |
| 0 | S | H | H | H | H | CH₃ | CH₃ | N | |
| 0 | S | H | H | H | H | CH₃ | OCH₃ | N | |
| 0 | S | H | H | H | H | OCH₃ | OCH₃ | N | |
| 0 | SO₂ | H | H | H | H | CH₃ | CH₃ | CH | |
| 0 | SO₂ | H | H | H | H | CH₃ | OCH₃ | CH | |
| 0 | SO₂ | H | H | H | H | OCH₃ | OCH₃ | CH | |
| 0 | SO₂ | H | H | H | H | CH₃ | CH₃ | N | |
| 0 | SO₂ | H | H | H | H | CH₃ | OCH₃ | N | |
| 0 | SO₂ | H | H | H | H | OCH₃ | OCH₃ | N | |
| 0 | S | H | H | CH₃ | H | CH₃ | CH₃ | CH | |
| 0 | S | H | H | CH₃ | H | CH₃ | OCH₃ | CH | |
| 0 | S | H | H | CH₃ | H | OCH₃ | OCH₃ | CH | |
| 0 | S | H | H | CH₃ | H | CH₃ | CH₃ | N | |
| 0 | S | H | H | CH₃ | H | CH₃ | OCH₃ | N | |
| 0 | S | H | H | CH₃ | H | OCH₃ | OCH₃ | N | |
| 0 | SO₂ | H | H | CH₃ | H | CH₃ | CH₃ | CH | |
| 0 | SO₂ | H | H | CH₃ | H | CH₃ | OCH₃ | CH | |
| 0 | SO₂ | H | H | CH₃ | H | OCH₃ | OCH₃ | CH | |
| 0 | SO₂ | H | H | CH₃ | H | CH₃ | CH₃ | N | |
| 0 | SO₂ | H | H | CH₃ | H | CH₃ | OCH₃ | N | |
| 0 | SO₂ | H | H | CH₃ | H | OCH₃ | OCH₃ | N | |
| 1 | S | H | H | H | H | CH₃ | CH₃ | CH | |
| 1 | S | H | H | H | H | CH₃ | OCH₃ | CH | |
| 1 | S | H | H | H | H | OCH₃ | OCH₃ | CH | |
| 1 | S | H | H | H | H | CH₃ | CH₃ | N | |
| 1 | S | H | H | H | H | CH₃ | OCH₃ | N | |
| 1 | S | H | H | H | H | OCH₃ | OCH₃ | N | |
| 1 | SO₂ | H | H | H | H | CH₃ | CH₃ | CH | |
| 1 | SO₂ | H | H | H | H | CH₃ | OCH₃ | CH | |
| 1 | SO₂ | H | H | H | H | OCH₃ | OCH₃ | CH | |
| 1 | SO₂ | H | H | H | H | CH₃ | CH₃ | N | |
| 1 | SO₂ | H | H | H | H | CH₃ | OCH₃ | N | |
| 1 | SO₂ | H | H | H | H | OCH₃ | OCH₃ | N | |
| 1 | S | H | H | CH₃ | H | CH₃ | CH₃ | CH | |
| 1 | S | H | H | CH₃ | H | CH₃ | OCH₃ | CH | |
| 1 | S | H | H | CH₃ | H | OCH₃ | OCH₃ | CH | |
| 1 | S | H | H | CH₃ | H | CH₃ | CH₃ | N | |
| 1 | S | H | H | CH₃ | H | CH₃ | OCH₃ | N | |
| 1 | S | H | H | CH₃ | H | OCH₃ | OCH₃ | N | |
| 1 | SO₂ | H | H | CH₃ | H | CH₃ | CH₃ | CH | |
| 1 | SO₂ | H | H | CH₃ | H | CH₃ | OCH₃ | CH | |
| 1 | SO₂ | H | H | CH₃ | H | OCH₃ | OCH₃ | CH | |
| 1 | SO₂ | H | H | CH₃ | H | CH₃ | CH₃ | N | |
| 1 | SO₂ | H | H | CH₃ | H | CH₃ | OCH₃ | N | |
| 1 | SO₂ | H | H | CH₃ | H | OCH₃ | OCH₃ | N | |
| 0 | SO₂ | CH₃ | H | CH₃ | H | OCH₃ | OCH₃ | N | |
| 0 | S | H | CH₃ | H | H | OCH₃ | OCH₃ | CH | |
| 0 | S | H | Cl | CH₃ | H | OCH₃ | OCH₃ | CH | |
| 0 | SO₂ | H | Br | H | H | OCH₃ | OCH₃ | CH | |
| 0 | S | H | CO₂CH₃ | CH₃ | H | OCH₃ | OCH₃ | CH | |
| 0 | S | H | CO₂CH₂CH₃ | H | H | OCH₃ | OCH₃ | CH | |
| 0 | SO₂ | H | CO₂CH₂CH₂CH₃ | CH₃ | H | CH₃ | OCH₃ | N | |
| 0 | S | H | CO₂CH(CH₃)₂ | H | H | OCH₃ | OCH₃ | N | |
| 0 | S | H | CO₂CH₂CH=CH₂ | CH₃ | H | OCH₃ | OCH₃ | CH | |
| 0 | SO₂ | H | CO₂CH₂CH₂OCH₃ | H | H | OCH₃ | OCH₃ | CH | |
| 0 | S | H | CO₂CH₂CH₂Cl | CH₃ | H | OCH₃ | OCH₃ | N | |
| 0 | S | H | SO₂CH₃ | H | H | OCH₃ | OCH₃ | N | |
| 0 | SO₂ | H | SO₂CH₂CH₂CH₃ | CH₃ | H | CH₃ | OCH₃ | CH | |

TABLE IIIa-continued

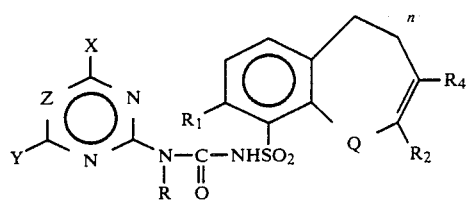

| n | Q | R | R₁ | R₂ | R₄ | X | Y | Z | m.p.(°) |
|---|---|---|---|---|---|---|---|---|---|
| 0 | S | H | SO₂CH(CH₃)₂ | H | H | OCH₃ | OCH₃ | CH | |
| 0 | S | H | OSO₂CH₃ | CH₃ | H | CH₃ | OCH₃ | N | |
| 0 | SO₂ | H | OSO₂CF₃ | H | H | OCH₃ | OCH₃ | N | |
| 0 | S | H | OSO₂CH(CH₃)₂ | H | H | CH₃ | OCH₃ | CH | |
| 0 | SO₂ | H | SO₂N(CH₃)₂ | CH₃ | H | OCH₃ | OCH₃ | CH | |
| 0 | SO₂ | H | SO₂N(CH₂CH₃)₂ | H | H | CH₃ | OCH₃ | N | |
| 0 | SO₂ | H | SO₂N(CH₃)CH₂CH₃ | CH₃ | H | OCH₃ | OCH₃ | N | |
| 0 | S | H | H | CH₂CH₃ | H | OCH₃ | OCH₃ | N | |
| 0 | SO₂ | H | H | CH₂CH₂CH₃ | H | CH₃ | OCH₃ | CH | |
| 0 | S | H | H | CH(CH₃)₂ | H | OCH₃ | OCH₃ | CH | |
| 0 | S | H | H | H | H | Cl | OCH₃ | CH | |
| 0 | SO₂ | H | H | CH₃ | H | CH₃ | NH₂ | CH | |
| 0 | S | H | H | H | H | CH₃ | NHCH₃ | CH | |
| 0 | S | H | H | CH₃ | H | CH₃ | N(CH₃)₂ | CH | |
| 0 | SO₂ | H | H | H | H | CH₃ | OC₂H₅ | CH | |
| 0 | S | H | H | CH₃ | H | CH₃ | OCH₂CH₃ | N | |
| 0 | S | H | H | H | H | OCH₃ | CH₂OCH₃ | CH | |

TABLE IIIb

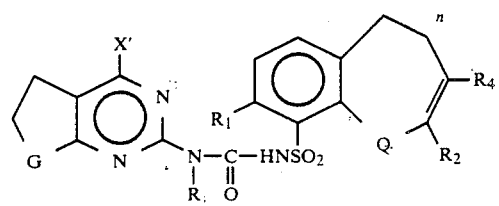

| n | Q | R | R₁ | R₂ | R₄ | X' | G |
|---|---|---|---|---|---|---|---|
| 0 | SO₂ | H | H | H | H | CH₃ | CH₂ |
| 0 | SO₂ | H | H | H | H | OCH₃ | CH₂ |
| 0 | SO₂ | H | H | H | H | OCH₂CH₃ | CH₂ |
| 0 | SO₂ | H | H | H | H | CH₃ | O |
| 0 | SO₂ | H | H | H | H | OCH₃ | O |
| 0 | SO₂ | H | H | H | H | OCH₂CH₃ | O |
| 0 | SO₂ | H | H | H | CH₃ | OCH₃ | O |
| 0 | S | H | H | CH₃ | H | OCH₃ | O |
| 0 | SO₂ | H | H | H | H | OCH₃ | O |
| 0 | S | H | CH₃ | CH₃ | H | OCH₃ | O |
| 0 | SO₂ | H | OCH₃ | CH₃ | H | OCH₃ | O |
| 0 | S | H | Cl | CH₃ | H | OCH₃ | O |
| 0 | SO₂ | H | Br | CH₃ | H | OCH₃ | O |
| 0 | S | H | CO₂CH₃ | CH₃ | H | OCH₃ | O |
| 0 | SO₂ | H | SO₂CH₃ | CH₃ | H | OCH₃ | O |
| 0 | S | H | OSO₂CH₃ | CH₃ | H | OCH₃ | O |
| 0 | SO₂ | H | SO₂N(CH₃)₂ | CH₃ | H | OCH₃ | O |
| 1 | SO₂ | H | H | H | H | OCH₃ | O |

TABLE IIIc

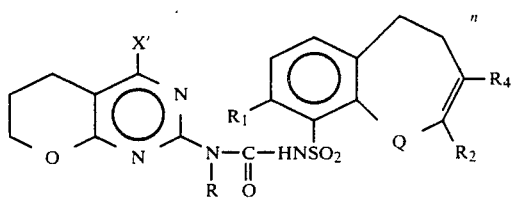

| n | Q | R | R₁ | R₂ | R₄ | X' |
|---|---|---|---|---|---|---|
| 0 | SO₂ | H | H | H | H | CH₃ |
| 0 | SO₂ | H | H | H | H | OCH₃ |
| 0 | SO₂ | H | H | H | H | OCH₂CH₃ |

TABLE IIIc-continued

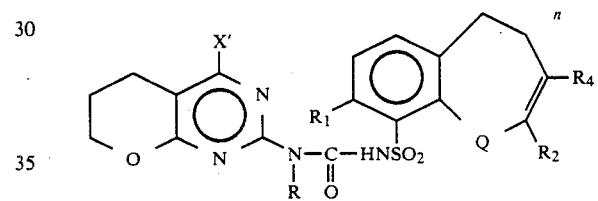

| n | Q | R | R₁ | R₂ | R₄ | X' |
|---|---|---|---|---|---|---|
| 0 | SO₂ | H | H | H | CH₃ | OCH₃ |
| 0 | S | H | H | CH₃ | H | OCH₃ |
| 0 | SO₂ | H | H | H | H | OCH₃ |
| 0 | S | H | CH₃ | CH₃ | H | OCH₃ |
| 0 | SO₂ | H | OCH₃ | CH₃ | H | OCH₃ |
| 0 | S | H | Cl | CH₃ | H | OCH₃ |
| 0 | SO₂ | H | Br | CH₃ | H | OCH₃ |
| 0 | S | H | CO₂CH₃ | CH₃ | H | OCH₃ |
| 0 | SO₂ | H | SO₂CH₃ | CH₃ | H | OCH₃ |
| 0 | S | H | OSO₂CH₃ | CH₃ | H | OCH₃ |
| 0 | SO₂ | H | SO₂N(CH₃)₂ | CH₃ | H | OCH₃ |
| 1 | SO₂ | H | H | H | H | OCH₃ |

TABLE IIId

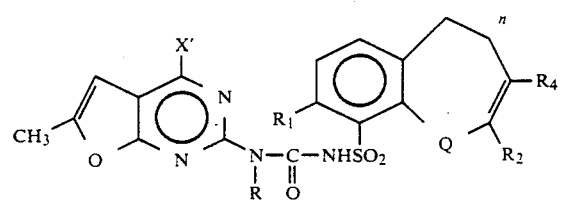

| n | Q | R | R₁ | R₂ | R₄ | X' |
|---|---|---|---|---|---|---|
| 0 | SO₂ | H | H | H | H | CH₃ |
| 0 | SO₂ | H | H | H | H | OCH₃ |
| 0 | SO₂ | H | H | H | H | OCH₂CH₃ |
| 0 | SO₂ | H | H | H | CH₃ | OCH₃ |
| 0 | S | H | H | CH₃ | H | OCH₃ |
| 0 | SO₂ | H | H | H | H | OCH₃ |
| 0 | S | H | CH₃ | CH₃ | H | OCH₃ |
| 0 | SO₂ | H | OCH₃ | CH₃ | H | OCH₃ |
| 0 | S | H | Cl | CH₃ | H | OCH₃ |

TABLE IIId-continued

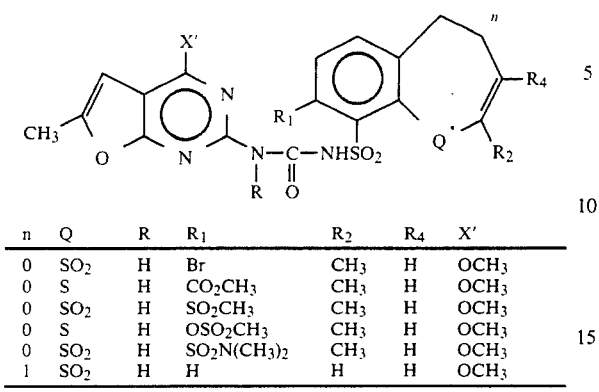

| n | Q | R | $R_1$ | $R_2$ | $R_4$ | X' |
|---|---|---|---|---|---|---|
| 0 | $SO_2$ | H | Br | $CH_3$ | H | $OCH_3$ |
| 0 | S | H | $CO_2CH_3$ | $CH_3$ | H | $OCH_3$ |
| 0 | $SO_2$ | H | $SO_2CH_3$ | $CH_3$ | H | $OCH_3$ |
| 0 | S | H | $OSO_2CH_3$ | $CH_3$ | H | $OCH_3$ |
| 0 | $SO_2$ | H | $SO_2N(CH_3)_2$ | $CH_3$ | H | $OCH_3$ |
| 1 | $SO_2$ | H | H | H | H | $OCH_3$ |

TABLE IVa

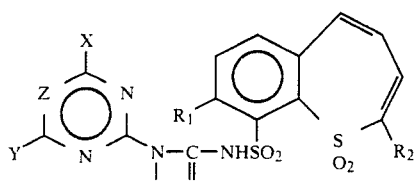

| R | $R_1$ | $R_2$ | X | Y | Z | m.p.(°) |
|---|---|---|---|---|---|---|
| H | H | H | $CH_3$ | $CH_3$ | CH | |
| H | H | H | $CH_3$ | $OCH_3$ | CH | |
| H | H | H | $OCH_3$ | $OCH_3$ | CH | |
| H | H | H | $CH_3$ | $CH_3$ | N | |
| H | H | H | $CH_3$ | $OCH_3$ | N | |
| H | H | H | $OCH_3$ | $OCH_3$ | N | |
| $CH_3$ | H | H | $OCH_3$ | $OCH_3$ | N | |
| H | H | $CH_3$ | $CH_3$ | $CH_3$ | CH | |
| H | H | $CH_3$ | $CH_3$ | $OCH_3$ | CH | |
| H | H | $CH_3$ | $OCH_3$ | $OCH_3$ | CH | |
| H | H | $CH_3$ | $CH_3$ | $CH_3$ | N | |
| H | H | $CH_3$ | $CH_3$ | $OCH_3$ | N | |
| H | H | $CH_3$ | $OCH_3$ | $OCH_3$ | N | |
| H | H | $CH_2CH_3$ | $CH_3$ | $OCH_3$ | CH | |
| H | H | $CH_2CH_2CH_3$ | $OCH_3$ | $OCH_3$ | CH | |
| H | H | $CH(CH_3)_2$ | $CH_3$ | $OCH_3$ | CH | |
| H | $OCH_3$ | H | $CH_3$ | $OCH_3$ | N | |
| H | Cl | H | $OCH_3$ | $OCH_3$ | N | |
| H | Br | H | $CH_3$ | $OCH_3$ | CH | |
| H | $CO_2CH_3$ | H | $OCH_3$ | $OCH_3$ | CH | |
| H | $SO_2CH_3$ | H | $CH_3$ | $OCH_3$ | N | |
| H | $OSO_2CH_3$ | H | $OCH_3$ | $OCH_3$ | N | |
| H | $SO_2N(CH_3)_2$ | H | $CH_3$ | $OCH_3$ | CH | |
| H | H | H | Cl | $OCH_3$ | CH | |
| H | H | H | $OCH_3$ | $OCH_3CH_3$ | CH | |
| H | H | H | $OCH_3$ | $CH_2OCH_3$ | CH | |
| H | H | H | $OCH_3$ | $NH_2$ | CH | |
| H | H | H | $OCH_3$ | $NHCH_3$ | CH | |
| H | H | H | $OCH_3$ | $N(CH_3)_2$ | CH | |
| H | H | H | $OCH_3$ | | $CH_2$ | |

TABLE IVb

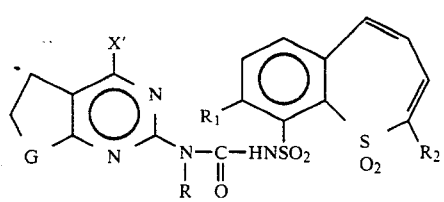

| R | $R_1$ | $R_2$ | X' | G |
|---|---|---|---|---|
| H | H | H | $CH_3$ | O |
| H | H | H | $OCH_3$ | O |
| H | H | H | $OCH_2CH_3$ | O |
| H | H | $CH_3$ | $OCH_3$ | O |

TABLE IVb-continued

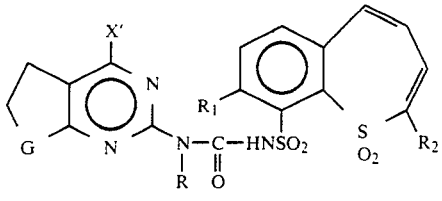

| R | $R_1$ | $R_2$ | X' | G |
|---|---|---|---|---|
| $CH_3$ | H | H | $OCH_3$ | O |
| H | $OCH_3$ | H | $OCH_3$ | O |
| H | Cl | H | $OCH_3$ | O |
| H | Br | H | $OCH_3$ | O |
| H | $CO_2CH_3$ | H | $OCH_3$ | O |
| H | $SO_2CH_3$ | H | $OCH_3$ | O |
| H | $OSO_2CH_3$ | H | $OCH_3$ | O |
| H | $SO_2N(CH_3)_2$ | H | $OCH_3$ | O |

TABLE IVc

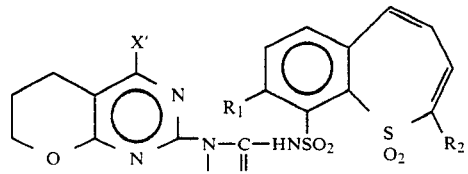

| R | $R_1$ | $R_2$ | X' |
|---|---|---|---|
| H | H | H | $CH_3$ |

TABLE IVc-continued

[Structure: chromene-fused pyrimidine with X' substituent, linked via N-C(=O)-N(R)-HNSO$_2$ to benzene ring with R$_1$, methyl, and vinyl substituents, and SO$_2$R$_2$ group]

| R | R$_1$ | R$_2$ | X' |
|---|---|---|---|
| H | H | H | OCH$_3$ |
| H | H | H | OCH$_2$CH$_3$ |
| H | H | CH$_3$ | OCH$_3$ |
| CH$_3$ | H | H | OCH$_3$ |
| H | OCH$_3$ | H | OCH$_3$ |
| H | Cl | H | OCH$_3$ |
| H | Br | H | OCH$_3$ |
| H | CO$_2$CH$_3$ | H | OCH$_3$ |
| H | SO$_2$CH$_3$ | H | OCH$_3$ |
| H | OSO$_2$CH$_3$ | H | OCH$_3$ |
| H | SO$_2$N(CH$_3$)$_2$ | H | OCH$_3$ |

TABLE IVd

[Structure: methyl-substituted furo-pyrimidine with X' substituent, linked via N-C(=O)-N(R)-HNSO$_2$ to benzene ring with R$_1$, methyl, and vinyl substituents, and SO$_2$R$_2$ group]

| R | R$_1$ | R$_2$ | X' |
|---|---|---|---|
| H | H | H | CH$_3$ |
| H | H | H | OCH$_3$ |
| H | H | H | OCH$_2$CH$_3$ |
| H | H | CH$_3$ | OCH$_3$ |
| CH$_3$ | H | H | OCH$_3$ |
| H | OCH$_3$ | H | OCH$_3$ |
| H | Cl | H | OCH$_3$ |
| H | Br | H | OCH$_3$ |
| H | CO$_2$CH$_3$ | H | OCH$_3$ |
| H | SO$_2$CH$_3$ | H | OCH$_3$ |
| H | OSO$_2$CH$_3$ | H | OCH$_3$ |
| H | SO$_2$N(CH$_3$)$_2$ | H | OCH$_3$ |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE V

| | Active Ingredient | Weight Percent* Diluent(s) | Surfactant(s) |
|---|---|---|---|
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138-140, 162-164, 166, 167 and 169-182;

H. Gysin and E. Knusli, U.S. Pat. No. 2,891,855, June 23, 1959, Col. 3, line 66 through Col. 5, line 17 and Examples 1-4;

G. C. Klingman, "Weed Control as a Science", John Wiley & Sons, Inc., New York, 1961, pp. 81-96; and J. D. Fryer and S. A. Evans, "Weed Control Handbook", 5th Ed., Blackwell Scientific Publications, Oxford, 1968, pp. 101-103.

In the following examples, all parts are by weight unless otherwise indicated.

EXAMPLE 8

| Wettable Powder | |
|---|---|
| N—[(4-methoxy-6-methylpyrimidin-2-yl)aminocarbonyl]-3,4-dihydro-2H—1-benzothiopyran-8-sulfonamide, 1,1-dioxide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 9

| Wettable Powder | |
|---|---|
| N—[(4,6-dimethoxypyrimidin-2-yl)aminocarbonyl]-3,4-dihydro-2H—1-benzothiopyran-8-sulfonamide, 1,1-dioxide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 10

| Granule | |
|---|---|
| Wettable Powder of Example 9 | 5% |
| attapulgite granules (U.S.S. 20-40 mesh; 0.84-0.42 mm) | 95% |

A slurry of wettable powder containing ≈25% solids is sprayed on the surface of attapulgite granules in a double-cone blender. The granules are dried and packaged.

EXAMPLE 11

| Extruded Pellet | |
|---|---|
| N—[(4-methoxy-6-methyl-1,3,5-triazin-2-yl)aminocarbonyl]-3,4-dihydro-2H—1-benzothiopyran-8-sulfonamide, 1,1-dioxide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 12

| Oil Suspension | |
|---|---|
| N—[(4-methoxy-6-methylpyrimidin-2-yl)aminocarbonyl]-3,4-dihydro-2H—1-benzothiopyran-8-sulfonamide, 1,1-dioxide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 13

| Wettable Powder | |
|---|---|
| N—[(4,6-dimethoxypyrimidin-2-yl)aminocarbonyl]-3,4-dihydro-2H—1-benzothiopyran-8-sulfonamide, 1,1-dioxide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 14

| Low Strength Granule | |
|---|---|
| N—[(4-methoxy-6-methylpyrimidin-2-yl)aminocarbonyl]-3,4-dihydro-2H—1-benzothiopyran-8-sulfonamide, 1,1-dioxide | 1% |
| N,N—dimethylformamide | 9% |
| attapulgite granules (U.S.S. 20-40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 15

| Aqueous Suspension | |
|---|---|
| N—[(4-methoxy-6-methyl-1,3,5-triazin-2-yl)aminocarbonyl]-3,4-dihydro-2H—1-benzothiopyran-8-sulfonamide, 1,1-dioxide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 16

| Solution | |
|---|---|
| N—[(4,6-dimethoxypyrimidin-2-yl)aminocarbonyl]-3,4-dihydro-2H—1-benzothiopyran-8-sulfonamide, 1,1- | 5% |

| Solution | |
|---|---|
| dioxide, sodium salt | |
| water | 95% |

The salt is added directly to the water with stirring to produce the solution, which may then be packaged for use.

EXAMPLE 17

| Low Strength Granule | |
|---|---|
| N—[(4-methoxy-6-methyl-1,3,5-triazine-2-yl)aminocarbonyl]-3,4-dihydro-2H—1-benzothiopyran-8-sulfonamide, 1,1-dioxide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 18

| Granule | |
|---|---|
| N—[(4-methoxy-6-methyl-1,3,5-triazin-2-yl)aminocarbonyl]-3,4-dihydro-2H—1-benzothiopyran-8-sulfonamide, 1,1-dioxide | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 19

| High Strength Concentrate | |
|---|---|
| N—[(4-methoxy-6-methylpyrimidin-2-yl)aminocarbonyl]-3,4-dihydro-2H—1-benzothiopyran-8-sulfonamide, 1,1-dioxide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 20

| Wettable Powder | |
|---|---|
| N—[(4,6-dimethoxypyrimidin-2-yl)aminocarbonyl]-3,4-dihydro-2H—1-benzothiopyran-8-sulfonamide, 1,1-dioxide | 90% |
| dioctyl sodium sulfosuccinate | 0.1% |
| synthetic fine silica | 9.9% |

The ingredients are blended and ground in a hammermill to produce particles essentially all below 100 microns. The material is sifted through a U.S.S. No. 50 screen and then packaged.

EXAMPLE 21

| Wettable Powder | |
|---|---|
| N—[(4-methoxy-6-methyl-1,3,5-triazin-2-yl)aminocarbonyl]-3,4-dihydro-2H—1-benzothiopyran-8-sulfonamide, 1,1-dioxide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 22

| Oil Suspension | |
|---|---|
| N—[(4,6-dimethoxypyrimidin-2-yl)aminocarbonyl]-3,4-dihydro-2H—1-benzothiopyran-8-sulfonamide, 1,1-dioxide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 23

| Dust | |
|---|---|
| N—[(4-methoxy-6-methylpyrimidin-2-yl)aminocarbonyl]-3,4-dihydro-2H—1-benzothiopyran-8-sulfonamide, 1,1-dioxide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

UTILITY

The compounds of the present invention are active herbicides. They have utility for broadspectrum pre- and/or post-emergence weed control in areas where complete control of all vegetation is desired, such as around fuel storage tanks, ammunition depots, industrial storage areas, parking lots, drivein theaters, around billboards, highway and railroad structures. Alternatively, the compounds may be used to modify plant growth.

The rates of application for the compounds of the invention are determined by a number of factors, including their use as growth modifiers, the crop species involved, the types of weeds to be controlled, weather and climate, formulations selected, mode of application, amount of foliage present, etc. In general terms, the subject compounds should be applied at levels of around 0.125 to 10 kg/ha, the lower rates being suggested for use on lighter soils and/or those having a low organic matter content, for growth modification or for situations where only short-term persistence is required.

The compounds of the invention may be used in combination with any other commercial herbicide examples of which are those of triazine, triazole, uracil, urea, amide, diphenylether, carbamate and bipyridylium types.

The herbicidal properties of the subject compounds were discovered in a number of greenhouse tests. The test procedures and results follow.

TEST A

Seeds of crabgrass (Digitaria sp.), barnyardgrass (*Echinochloa crusgalli*), wild oats (*Avena fatua*), sicklepod (*Cassia obtusifolia*), morningglory (Ipomoea sp.), cocklebur (Xanthium sp.), sorghum, corn, soybean, sugar beet, rice, wheat and nutsedge tubers (*Cyperus rotundus*) were planted in a growth medium and treated pre-emergence with the chemicals dissolved in a non-phytotoxic solvent. At the same time, these crop and weed species, along with cotton and bush bean, were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
E=emergence inhibition;
G=growth retardation;
H=formative effects;
U=unusual pigmentation;
X=axillary stimulation; and
6Y=abscised buds or flowers.

Compounds

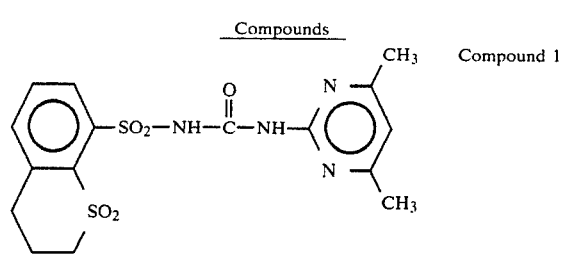
Compound 1

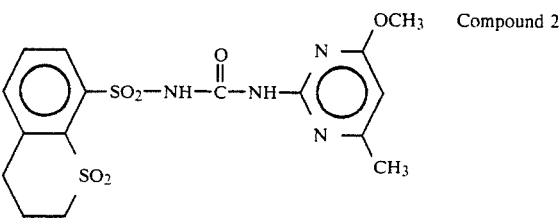
Compound 2

-continued
Compounds

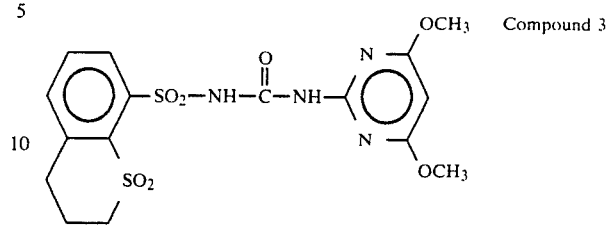
Compound 3

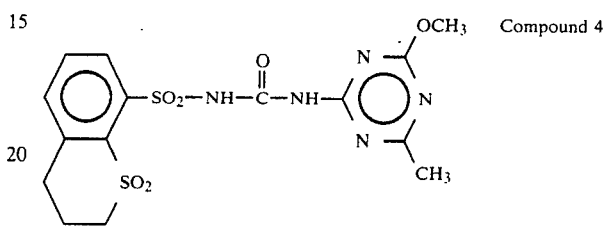
Compound 4

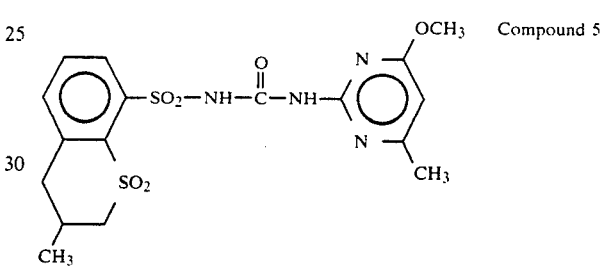
Compound 5

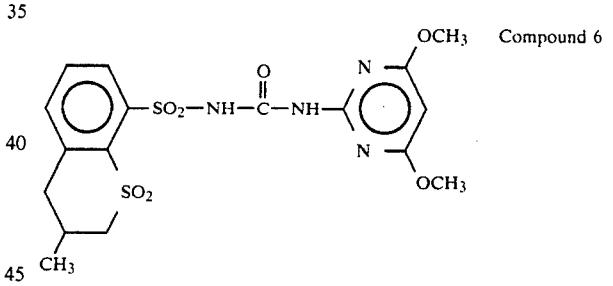
Compound 6

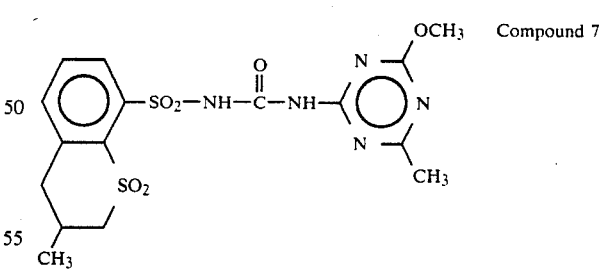
Compound 7

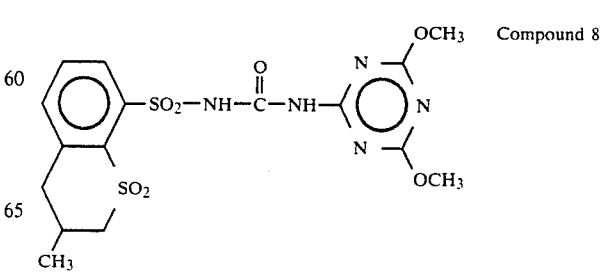
Compound 8

TABLE A

| Rate, kg/ha | Cmpd. 1<br>0.05 | Cmpd. 2<br>0.05 | Cmpd. 3<br>0.05 | Cmpd. 4<br>0.05 | Cmpd. 4<br>0.4 | Cmpd. 5<br>0.05 | Cmpd. 5<br>2 | Cmpd. 6<br>0.05 | Cmpd. 6<br>2 |
|---|---|---|---|---|---|---|---|---|---|
| POST-EMERGENCE | | | | | | | | | |
| Bush bean | 3C,6Y | 5C,9G,6Y | 5C,9G,6Y | 5C,8G,6Y | 4C,8G,6Y | 0 | 1C | 0 | 0 |
| Cotton | 1C | 2C,5G | 2C,4G | 2C,6G | 4C,8G | 0 | 2C | 0 | 1C |
| Morningglory | 2C | 5C,9G | 5C,9G | 2C,5G | 4C,5H | 0 | 3C | 0 | 1C |
| Cocklebur | 1C | 5C,9G | 5C,9G | 1H | 4C,8H | 0 | 2C | 0 | 1C |
| Sicklepod | 1C | 4C,8G | 5C,9G | 0 | 1C | 0 | 0 | 0 | 0 |
| Nutsedge | 0 | 1C | 1C,5G | 0 | 0 | 0 | 0 | 0 | 0 |
| Crabgrass | 0 | 4C,6G | 5C,9G | 2G | 3C,8G | 0 | 2C,3G | 0 | 2C,4G |
| Barnyardgrass | 1C,3H | 5C,9H | 5C,9H | 8H | 5C,8H | 0 | 2C | 0 | 1C |
| Wild Oats | 0 | 5C,9G | 5C,9G | 2C,8G | 4C,8G | 0 | 0 | 0 | 0 |
| Wheat | 1C | 2C,9G | 4C,9G | 2C,8G | 4U,9G | 0 | 0 | 0 | 0 |
| Corn | 0 | 3C,9G | 4C,9G | 3C,9G | 3U,9G | 0 | 3C,4G | 0 | 0 |
| Soybean | 1C | 4C,9G,5X | 3C,8G | 2C,3H | 2C,7G | 0 | 2C | 0 | 1C |
| Rice | 2G | 5C,9G | 6C,9G | 5C,9G | 5C,9G | 0 | 3C | 0 | 2C,5G |
| Sorghum | 1C,4G | 4C,9G | 1C,9G | 3C,9G | 2C,9G | 0 | 3C,5G | 0 | 2C,5H |
| Sugar beet | 2C,4G | 4C,8G | 9C | 2C,3H | 3C,3H | 0 | 3C | 0 | 1C |

| Rate, kg/ha | Cmpd. 7<br>0.05 | Cmpd. 7<br>2 | Cmpd. 8<br>0.05 | Cmpd. 8<br>2 |
|---|---|---|---|---|
| POST-EMERGENCE | | | | |
| Bush bean | 0 | 1C | 0 | 0 |
| Cotton | 0 | 4C,4H | 0 | 1C |
| Morningglory | 0 | 2C,2H | 0 | 0 |
| Cocklebur | 0 | 1C,5G | 0 | 2G |
| Sicklepod | 0 | 1C | 0 | 0 |
| Nutsedge | 0 | 0 | 0 | 0 |
| Crabgrass | 0 | 3C,6G | 0 | 0 |
| Barnyardgrass | 0 | 3C,9H | 0 | 0 |
| Wild Oats | 0 | 2C,8G | 0 | 0 |
| Wheat | 0 | 2C,7G | 0 | 0 |
| Corn | 0 | 2C,8H | 0 | 2G |
| Soybean | 0 | 0 | 0 | 0 |
| Rice | 0 | 2C,8G | 0 | 0 |
| Sorghum | 0 | 2C,9G | 0 | 1C |
| Sugar beet | 0 | 1C | 0 | 0 |

| Rate, kg/ha | Cmpd. 1<br>0.05 | Cmpd. 2<br>0.05 | Cmpd. 3<br>0.05 | Cmpd. 4<br>0.05 | Cmpd. 4<br>0.4 | Cmpd. 5<br>0.05 | Cmpd. 5<br>2 | Cmpd. 6<br>0.05 | Cmpd. 6<br>2 |
|---|---|---|---|---|---|---|---|---|---|
| PRE-EMERGENCE | | | | | | | | | |
| Morningglory | 0 | 4C,6H | 9G | 2C | 4C,6H | 0 | 2C,7H | 0 | 8G |
| Cocklebur | 0 | 9H | 9H | — | 9H | 0 | 8H | 0 | 8H |
| Sicklepod | 0 | 3C | 2C,8G | 0 | 3C,6G | 0 | 3C | 0 | 2C,6G |
| Nutsedge | 0 | 1C | 2C,3G | 0 | 0 | 0 | 2C,7G | 0 | 8G |
| Crabgrass | 0 | 2C,4G | 2C,5G | 0 | 1C,5G | 0 | 2C,4G | 0 | 2G |
| Barnyardgrass | 0 | 2C,5G | 3C,9H | 1C | 2C,8G | 0 | 3C,8H | 0 | 2C,8H |
| Wild Oats | 0 | 4C,6G | 5C,9G | 1C,4G | 4C,9G | 0 | 4C,8G | 0 | 2C,9G |
| Wheat | 0 | 3C,9G | 2C,9H | 1C,5G | 3C,9G | 0 | 2C,8G | 0 | 2C,9G |
| Corn | 0 | 4C,8G | 3C,9G | 2C,4G | 2C,9G | 0 | 3C,9H | 0 | 2C,8G |
| Soybean | 0 | 3C,2H | 3C,3H | 2G | 2C,3H | 0 | 2C,2H | 0 | 2C,2H |
| Rice | 0 | 2C,3G | 10E | 2C,4G | 10E | 0 | 4C,9H | 0 | 5C,9H |
| Sorghum | 0 | 5C,9H | 5C,9G | 2C,8G | 9H | 0 | 4C,9G | 0 | 2C,9G |
| Sugar beet | 0 | 2C,4G | 10E | 3C,8G | 7G | 0 | 5C,9G | 0 | 4C,8G |

| Rate, kg/ha | Cmpd. 7<br>0.05 | Cmpd. 7<br>2 | Cmpd. 8<br>0.05 | Cmpd. 8<br>2 |
|---|---|---|---|---|
| PRE-EMERGENCE | | | | |
| Morningglory | 0 | 8H | 0 | 2C,7H |
| Cocklebur | 0 | 9H | 0 | 9H |
| Sicklepod | 0 | 0 | 0 | 1C |
| Nutsedge | 0 | 3G | 0 | 10E |
| Crabgrass | 0 | 0 | 0 | 1C |
| Barnyardgrass | 0 | 3C,9H | 0 | 2C,3H |
| Wild Oats | 0 | 2C,5G | 0 | 0 |
| Wheat | 0 | 2C,9G | 0 | 3G |
| Corn | 0 | 2C,8G | 0 | 3C,6H |
| Soybean | 0 | 1C | 0 | 0 |
| Rice | 0 | 9H | 0 | 8H |
| Sorghum | 0 | 3C,9G | 0 | 2C,9G |
| Sugar beet | 0 | 5G | 0 | 4G |

TEST B

Two plastic bulb pans were filled with fertilized and limed Woodstown sandy loam. One pan was planted with corn, sorghum, Kentucky bluegrass and several grass weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica*

*arvensis*), cocklebur (*Xanthium pensylvanicum*), morningglory (*Ipomoea hederacea*), sicklepod (*Cassia obtusifolia*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugar beets. The above four containers were treated pre-emergence with several test compounds within the scope of the invention.

Twenty-eight days after treatment, the plants were evaluated and visually rated for response to the chemical treatments utilizing the rating system described previously for Test A. The data are summarized in Table B.

TABLE B
PRE-EMERGENCE ON WOODSTOWN SANDY LOAM

| Rate, kg/ha | Compound 2 | | Compound 3 | | Compound 4 | |
|---|---|---|---|---|---|---|
| | 0.03 | 0.12 | 0.03 | 0.12 | 0.06 | 0.25 |
| Crabgrass | 0 | 2G | 0 | 3G | 0 | 0 |
| Barnyardgrass | 0 | 2G | 2G | 3G | Oats | 2G |
| Sorghum | 0 | 8G | 6G | 9G | 8G | 9G |
| Wild Oats | 0 | 4G | 2G | 8G | 5G | 8G |
| Johnsongrass | 0 | 4G | 7G | 9G | 4G | 8G |
| Dallisgrass | 0 | 2G | 0 | 9G | 0 | 5G |
| Giant foxtail | 0 | 5G | 0 | 8G | 4G | 6G |
| Ky. bluegrass | 0 | 8G | 7G | 9G | 5G | 9G |
| Cheatgrass | 0 | 7G | 6G | 9G | 4G | 8G |
| Sugar beets | 0 | 5G | 2G | 7G | 3G | 5G |
| Corn | 0 | 2G | 2G | 7G | 2G | 8G |
| Mustard | 0 | 7G | 3G | 9G | 8G | 9G |
| Cocklebur | 0 | 2G | 0 | 2G | 0 | 3G |
| Pigweed | — | — | — | — | — | — |
| Nutsedge | 0 | 0 | 0 | 2G | 4G | 6G |
| Cotton | 0 | 0 | 0 | 2G | 0 | 0 |
| Morningglory | 0 | 0 | 0 | 6G | 0 | 0 |
| Sicklepod | 0 | 0 | 0 | 5G | 0 | 0 |
| Teaweed | 0 | 0 | 0 | 2G | 0 | 0 |
| Velvetleaf | 0 | 0 | 0 | 6G | 0 | 0 |
| Jimsonweed | 0 | 0 | 0 | 5G | 0 | 0 |
| Soybean | 0 | 0 | 0 | 0 | 0 | 0 |
| Rice | 2G | 9G | 8G | 10C | 9G | 9G |
| Wheat | 2G | 5G | 5G | 7G | 0 | 0 |

What is claimed is:

1. A compound of the formula:

$$JSO_2NHCNA$$
$$\underset{R}{|} \quad \underset{O}{\|}$$

wherein J is

[structures $J_1$, $J_2$, $J_3$, $J_4$, $J_5$, $J_6$, $J_7$]

Q is O, S or $SO_2$;
R is H or $CH_3$;
$R_1$ is H, $CH_3$, $OCH_3$, Cl, Br, $CO_2R_5$, $SO_2R_6$, $OSO_2R_7$ or $SO_2NR_8R_9$;
$R_4$ is H or $CH_3$;
$R_2$ and $R_3$ are independently H or $C_1$-$C_3$ alkyl;
$R_5$ is $C_1$-$C_3$ alkyl, $CH_2CH=CH_2$, $CH_2CH_2OCH_3$ or $CH_2CH_2Cl$ $R_6$ is $C_1$-$C_3$ alkyl;
$R_7$ is $C_1$-$C_3$ alkyl or $CF_3$;
$R_8$ and $R_9$ are independently $C_1$-$C_2$ alkyl;
A is

[structure with N, X, Y, Z]

X is $CH_3$, $OCH_3$ or Cl;
Y is $CH_3$, $OCH_3$, $OC_2H_5$, $CH_2OCH_3$, $C_2H_5$, $NH_2$, $NHCH_3$ or $N(CH_3)_2$;
Z is CH;
and their agriculturally suitable salts; provided that:
(1) when X is Cl, then Y is $OCH_3$, $NH_2$, $NHCH_3$, $N(CH_3)_2$ or $OC_2H_5$;
(2) the total number of carbon atoms in $R_2$ and $R_3$ are less than or equal to 3;
(3) in Formula $J_2$, when $R_2$ and $R_3$ are other than H, then $R_4$ is H;
(4) in Formula $J_3$, when $R_2$ is other than H, then $R_4$ is H;
(5) when Q is S, then $R_1$ is not $SO_2NR_8R_9$;
(6) in Formulae $J_3$ and $J_6$, Q may not be O; and
(7) in Formula $J_7$, $R_1$ is not $CH_3$.

2. Compounds of claim 1 where J is $J_1$.
3. Compounds of claim 2 where R is H.
4. Compounds of claim 3 where $R_1$ is H.
5. Compounds of claim 4 where A is

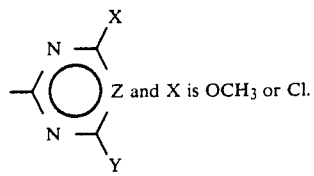

and X is OCH₃ or Cl.

6. Compounds of claim 5 where Y is CH₃ or OCH₃.
7. Compounds of claim 1 where J is J₂.
8. Compounds of claim 7 where R is H.
9. Compounds of claim 8 where R₁ is H.
10. Compounds of claim 9 where X is OCH₃ or Cl.
11. Compounds of claim 10 where Y is CH₃ or OCH₃.
12. Compounds of claim 1 where J is J₃.
13. Compounds of claim 12 where R is H.
14. Compounds of claim 13 where R₁ is H.
15. Compounds of claim 14 where X is OCH₃ or Cl.
16. Compounds of claim 15 where Y is CH₃ or OCH₃.
17. Compounds of claim 1 where J is J₄.
18. Compounds of claim 17 where R is H.
19. Compounds of claim 18 where R₁ is H.
20. Compounds of claim 19 where X is OCH₃ or Cl.
21. Compounds of claim 20 where Y is CH₃ or OCH₃.
22. Compounds of claim 1 where J is J₅.
23. Compounds of claim 22 where R is H.
24. Compounds of claim 23 where R₁ is H.
25. Compounds of claim 24 where X is OCH₃ or Cl.
26. Compounds of claim 25 where Y is CH₃ or OCH₃.
27. Compounds of claim 1 where J is J₆.
28. Compounds of claim 27 where R is H.
29. Compounds of claim 28 where R₁ is H.
30. Compounds of claim 29 where X is OCH₃ or Cl.
31. Compounds of claim 30 where Y is CH₃ or OCH₃.
32. Compounds of claim 1 where J is J₇.
33. Compounds of claim 32 where R is H.
34. Compounds of claim 33 where R₁ is H.
35. Compounds of claim 34 where X is OCH₃ or Cl.
36. Compounds of claim 35 where Y is CH₃ or OCH₃.
37. The compound of claim 1 which is N-[(4-methoxy-6-methylpyrimidin-2-yl)aminocarbonyl]-3,4-dihydro-2H-1-benzothiopyran-8-sulfonamide, 1,1-dioxide.
38. The compound of claim 1 which is N-[(4,6-dimethoxypyrimidin-2-yl)aminocarbonyl]-3,4-dihydro-2H-1-benzothiopyran-8-sulfonamide, 1,1-dioxide.
39. A composition suitable for controlling the growth of undesired vegetation which comprises an effective amount of a compound of claim 1 and at least one of the following: surfactant, solid or liquid diluent.
40. A composition suitable for controlling the growth of undesired vegetation which comprises an effective amount of a compound of claim 2 and at least one of the following: surfactant, solid or liquid diluent.
41. A composition suitable for controlling the growth of undesired vegetation which comprises an effective amount of a compound of claim 3 and at least one of the following: surfactant, solid or liquid diluent.
42. A composition suitable for controlling the growth of undesired vegetation which comprises an effective amount of a compound of claim 4 and at least one of the following: surfactant, solid or liquid diluent.
43. A composition suitable for controlling the growth of undesired vegetation which comprises an effective amount of a compound of claim 5 and at least one of the following: surfactant, solid or liquid diluent.
44. A composition suitable for controlling the growth of undesired vegetation which comprises an effective amount of a compound of claim 6 and at least one of the following: surfactant, solid or liquid diluent.
45. A composition suitable for controlling the growth of undesired vegetation which comprises an effective amount of a compound of claim 7 and at least one of the following: surfactant, solid or liquid diluent.
46. A composition suitable for controlling the growth of undesired vegetation which comprises an effective amount of a compound of claim 8 and at least one of the following: surfactant, solid or liquid diluent.
47. A method for controlling the growth of undesired vegetation which comprises applying to the locus to be protected an effective amount of a compound of claim 1.
48. A method for controlling the growth of undesired vegetation which comprises applying to the locus to be protected an effective amount of a compound of claim 2.
49. A method for controlling the growth of undesired vegetation which comprises applying to the locus to be protected an effective amount of a compound of claim 3.
50. A method for controlling the growth of undesired vegetation which comprises applying to the locus to be protected an effective amount of a compound of claim 4.
51. A method for controlling the growth of undesired vegetation which comprises applying to the locus to be protected an effective amount of a compound of claim 5.
52. A method for controlling the growth of undesired vegetation which comprises applying to the locus to be protected an effective amount of a compound of claim 6.
53. A method for controlling the growth of undesired vegetation which comprises applying to the locus to be protected an effective amount of a compound of claim 7.
54. A method for controlling the growth of undesired vegetation which comprises applying to the locus to be protected an effective amount of a compound of claim 8.

* * * * *